(12) United States Patent
Mallucci et al.

(10) Patent No.: US 7,994,113 B2
(45) Date of Patent: Aug. 9, 2011

(54) βGBP, COMPOSITIONS COMPRISING βGBP, AND RELATED METHODS AND USES THEREOF

(76) Inventors: Livio Mallucci, London (GB); Valerie Wells, London (GB)

( * ) Notice: Subject to any disclaimer, the term of this patent is extended or adjusted under 35 U.S.C. 154(b) by 338 days.

(21) Appl. No.: 12/157,923

(22) Filed: Jun. 13, 2008

(65) Prior Publication Data

US 2009/0017049 A1   Jan. 15, 2009

Related U.S. Application Data

(60) Provisional application No. 60/934,841, filed on Jun. 14, 2007.

(51) Int. Cl.
*C07K 14/00* (2006.01)

(52) U.S. Cl. .......................................... 514/1; 530/350

(58) Field of Classification Search ....... 514/1; 530/350
See application file for complete search history.

(56) References Cited

U.S. PATENT DOCUMENTS

| | | | | |
|---|---|---|---|---|
| 5,587,460 | A | * | 12/1996 | Nedwin et al. ................. 530/396 |
| 5,948,628 | A | * | 9/1999 | Cummings et al. ........... 435/7.24 |
| 6,127,169 | A | * | 10/2000 | Mallucci et al. ........... 435/320.1 |

FOREIGN PATENT DOCUMENTS

| | | |
|---|---|---|
| GB | 2249312 | 5/1992 |
| WO | WO 92/07938 | 5/1992 |

OTHER PUBLICATIONS

Horiguchi et al. 2003; Galectin-1 inducescell adhesion to the extracellular matrix and apoptosis of non-adherent human colon cncer Colo201 cells. J. Biochemistry 134(6): 869-874.*
Baatar, D. et al (2007) Journal of Immun vol. 178 pp. 1-2.
Blaser, C. et al (1998) Eur J Immunol 28: 2311-2319.
Johnstone, RW et al. (2002) Cell 108: 153-164.
Mallucci, L. et al. (2003). Biochem. Pharmacol vol. 66 pp. 1563-1569.
Mallucci, L. et al. J. (2004) Immunotherap. vol. 27 p. S55.
Mallucci, L. et al. (2005) Curr. Opinion Invest. Drugs vol. 6 pp. 1228-1233.
Mallucci, L. et al. (2006) Journal of Immunotherapy vol. 29 p. 675.
Mallucci, L. and Wells, (2007) *Apoptosis, Cell Signaling and Human Diseases: Molecular Mechanisms*, Humana Press p. 203-216.
Mazurek, N. et al (2007) Journal of Biol Chem pp. 1-25.
Rabinovich, GA et al. (1997) J. Biochem 122: 365-373.
Rabinovich, GA et al. (1998) J. Immunol. 160: 4831-4840.
Rabinovich, GA et al. (1999) J. Exp. Med. 190: 385-397.
Ravatn, R. et al. (2005) Cancer Res. vol. 65 pp. 1631-1634.
Spellacy, N. et al. (2002) Br. J. Cancer vol. 86 p. S21, Abs No. 4.3.
Tsuboi, K. et al (2007) Anticancer Research vol. 27 pp. 2289-2296.
Wells, V and Mallucci, L. (1991) Cell 64: 91-97.
Wells, V. et al (1999) Eur J. Cancer, vol. 35 pp. 978-983.
Wells, V. et al. (2002) Br. J. Cancer vol. 86 p. S85, Abs No. P167.
Wells, V. et al (2007) Oncogene vol. 26 pp. 7709-7714.

* cited by examiner

*Primary Examiner* — Karen Carlson
(74) *Attorney, Agent, or Firm* — Klauber & Jackson LLC

(57) ABSTRACT

The invention relates to β-galactoside binding protein (βGBP) and compositions, including pharmaceutical compositions, comprising βGBP for use in therapy and related applications. In particular, the invention relates to use of βGBP and the manufacture of medicaments for the treatment or prevention of conditions in which disease associated cell division occurs, wherein the cells which result from said disease associated cell division comprise a cell in respect of which the effect of βGBP is not inhibition of growth. The invention also relates to methods of inducing apoptosis, methods of treating or preventing conditions in which disease associated cell division occurs and methods of assessing the suitability of βGBP as a therapeutic agent.

27 Claims, 19 Drawing Sheets

βGBP, COMPOSITIONS COMPRISING βGBP, AND RELATED METHODS AND USES THEREOF

CROSS-REFERENCE TO RELATED APPLICATIONS

The present application claims priority of provisional application U.S. Ser. No. 60/934,841, filed on Jun. 14, 2007, the disclosure of which is incorporated by reference herein in its entirety. Applicants claim the benefits of such application under 35 U.S.C. §119(e).

FIELD OF THE INVENTION

The present invention relates to β-galactoside binding protein (βGBP) and compositions comprising βGBP for use in therapy and related applications. In particular, the invention relates to use of βGBP and the manufacture of medicaments for the treatment or prevention of conditions in which disease associated cell division occurs, wherein the cells which result from said disease associated cell division comprise a cell in respect of which the effect of βGBP is not inhibition of growth. The invention also relates to products and pharmaceutical compositions comprising βGBP. The use of βGBP to inhibit phosphatidylinositol-3-OH kinase (PI3 kinase, or PI3K) and to reduce the expression of the akt gene is also part of the present invention. The invention also relates to methods of inducing apoptosis, methods of treating or preventing conditions in which disease associated cell division occurs and methods of assessing the suitability of βGBP as a therapeutic agent.

BACKGROUND OF THE INVENTION

All documents to which reference is made herein are incorporated by reference in their entirety. βGBP is a negative cell cycle regulator (Wells V, Mallucci L 1991) with anti-cancer properties (Mallucci et al., 2003), recently identified as an anti-proliferative cytokine produced by activated CD4+ and CD8+ T cells (Blaser et al., 1998). It is also endogenously released by somatic cells. βGBP from several species has been cloned, expressed and purified. Thus, recombinant βGBP (for example human Hu-r-βGBP) is also available. All types of βGBP, irrespective of source, are simply referred to as βGBP herein.

βGBP is also known to induce programmed cell death (apoptosis) in cancer cells without harming normal cells. Thus βGBP enforces different regulatory functions in normal and cancer cells.

Cell division is a normal part of growth. It may also occur under other circumstances in a healthy individual, for example clonal expansion of lymphocytes during an immune reaction to a pathogen. However, if cell proliferation and growth is insufficiently controlled excessive cell division may occur. This excessive, or otherwise undesirable cell division may be considered to be disease associated cell division. Such cell division is a characteristic of hyperproliferative conditions.

One of the best known hyperproliferative conditions is cancer, although the term does encompass other conditions. These include self immune responses (such as autoimmune diseases) and immune responses against transplanted organs, tissues or cells (sometimes termed xeno reactions). Proliferation of activated T cells is involved in the pathology in many immune conditions mediated by undesirable cell division.

Cancer may result from a breakdown of the complex web of regulatory signals to which normal cells are subjected in healthy individuals. Under normal physiological conditions cells receive and respond to a wide range of stimuli, some favouring proliferation, some inhibiting proliferation. Similarly cells receive and respond to different stimuli that are either pro- or anti-apoptotic. In this manner a balance is preserved. Cell populations are replenished, replaced or expanded as necessary, but excessive proliferation is kept in check or apoptosis is enforced to maintain appropriate cell populations.

Owing to the highly complex nature of this regulation, and the many different effectors involved, the development of different cancer types and cancers in different individuals may result from a wide variety of changes or disturbances to the normal regulatory network.

As cancer develops, further mutations may accumulate in cancer cells, leading to greater disregulation of cellular functions. Selective pressure as the cancer cells divide tends to result in a stronger and stronger proliferative (or mitogentic) character and weaker response to anti-proliferative signals. Additionally, as cancer cells develop and become more aggressive, they may be forced to rely increasingly on survival signalling in order to overcome (and survive) an increase in the pro-apoptotic signalling which would normally remove such a cell from the population.

In addition, selective pressure brought about by the presence of chemotherapeutic agents leads to the development of drug resistance in many cancers.

In summary, cancers frequently result from an accumulation of mutations in a population of cells. The development of new mutations in individual cells and the inheritance of these mutations by new daughter cells typically results in a spectrum of cellular phenotypes and behaviours within a tumour or population of cancer cells.

These may range from less aggressive phenotypes (e.g. lower rates of division, greater sensitivity to normal physiological stimuli such as negative regulators of growth and pro-apoptopic signals), to more aggressive phenotypes, (e.g. higher rates of division, lower sensitivity (or the absence of sensitivity) to normal physiological stimuli such as negative regulators of growth and pro-apoptopic signals, reliance on survival signalling to avoid apoptosis, and increased drug resistance).

Selective pressure within such a population of cells tends to result in the development of increasing numbers of ever more aggressive cellular phenotypes as further mutations accumulate in the cells. Clones of cancer cells that are more aggressive and dividing more rapidly tend to out-compete less aggressive clones. Thus the character of the cancer overall tends to become more aggressive and therefore more serious and life threatening as time passes and further mutations accumulate.

Genetic alterations which in cancer cells magnify mitogenic signalling and are a cause of aggressive disease and resistance to therapies include amplification of the erbB2 (HER/neu) gene, present in many types of cancer and frequent in breast, ovarian and stomach carcinomas, and point mutations of the ras genes, common in about 15-20% of all tumors.

ErbB2 is a ligand-less member of the ErbB/EGF tyrosine kinase receptor family which magnifies mitogenic signalling by being constitutively active, by dimerising as a preferred partner with other ErbB members, which in breast cancer can be overexpressed, and by resisting endocytic degradation (Hynes et al., 1994, Yu and Hung 2000, Mendelsohn and Baselga 2000, Harari and Yarden 2000).

Phosphorylated tyrosine residues in the cytoplasmic tail of the ErbB2 molecule lead to the formation of high affinity binding sites for the SH2 domains of Shc and Grb2 adapter proteins (Segatto et al., 1990, Dankart et al., 1997), the binding of the nucleotide exchange factor SOS to the SH3 domains of Grb2, the conversion of GDP-Ras to active GTP-Ras and the activation of effector pathways which transduce proliferative, migratory and survival signalling (Mitin et al., 2005).

Ras proteins which harbour a single missense mutation magnify mitogenic signalling by chronically activating Raf serine/threonine kinases to force a phosphorylation cascade which enhances ERK activity and cell proliferation (Bos 1989, Downward 2003, Repasky et al., 2004). Critically, by interacting with the catalytic subunit of class IA (Rodriguez-Viciana et al., 1994) and class IB (Pacold et al., 2000, Walker et al., 2000 and Djodjevic et al., 2002) phosphatidylinositol-3-OH kinase (PI3 Kinase or PI3K), continuously activated Ras and constitutively active mutated Ras can contribute to coupling mitogenic input with survival ability.

By catalysing the conversion of phosphoinositide(4,5)P2 to phophoinositide(3,4,5)P3, PI3K allows Akt/PKB recruitment to the plasma membrane where Akt is activated. Phosphorylation of downstream targets such as Bad, caspase 9, forkhead transcription factors and IKKα by activated Akt confers resistance to apoptosis (Hennessy et al., 2005).

PI3K also regulates signalling networks that mediate cell growth (Foukas et al., 2006), cell proliferation (Wennstrom and Downward 1999), cytoskeletal organization (Rodriguez-Viciana et al., 1997), cell motility and migration (Vivanco and Sawyers 2002), all processes of central importance to the evolution of aggressive tumorigenesis.

The identification of multiple binding partners and downstream effectors of PI3K and of Ras has provided scope for the design of anticancer drugs specifically aimed at selected molecular targets (Downward 2003, Hennessy et al., 2005, Gibbs Chang et al., 2003 Luo J et al., 2003 and Baselga 2006), but questions have been raised concerning possible reasons for the as yet limited therapeutic success of these strategies. Concerns include the ability of intracellular signalling to integrate and bypass individual blocks, the possible molecular promiscuity of the targeting compound, lack of cell specificity, cytotoxicity and drug resistance (Johnstone et al., 2002, Mallucci et al., 2003 and Mallucci and Wells 2005).

Similarly to cancer, certain immune reactions may involve disease associated, i.e. undesirable cell division. For example, such cell division may occur among lymphocytes.

Autoimmunity is an example of an undesirable immune reaction which involves undesirable proliferation of lymphocytes such as T cells. Typically, these cells mediate immune reactions against endogenous targets within the individual concerned. The usual control mechanisms which should restrain activation and proliferation of such self reactive cells may for some reason break down in autoimmunity. Thus pathology results from the activities of a proliferating pool of cells targeting the self. The pool of proliferating lymphocytes in an autoimmune condition will typically comprise cells which are considered aggressive, or are dividing persistently. An example of an autoimmune condition is systemic lupus erythematosus (also known as SLE or lupus).

Alloimmunity is a condition that is related to autoimmunity. In alloimmune reactions the body gains immunity, from an exogenous source, e.g. another individual of the same species, against its own cells. Alloimmunity differs from autoimmunity since in the former condition the immune system attacks the body's own cells without being provoked or influenced by exogenous substances.

Alloimmunity may occur for example in the recipient of a transfusion of fluids such as blood or plasma, in the recipient of an allografts (grafts), or in the fetus after maternal antibodies have passed through the placenta into the fetus (e.g. in haemolytic disease of the newborn or fetomaternal alloimmune thrombocytopenia). Alloimmunity may be considered to be 'provoked autoimmunity'.

An alternative, but mechanistically related problem arises when biological components such as organs, tissues or cells (i.e. grafts) are transplanted between genetically distinct individuals, resulting in an immune reaction against the graft. Whole organs may be transplanted, alternatively portions of organs, or quantities of bone marrow (e.g. comprising progenitor cells) may be transferred from donor to recipient. It may also occur as a result of a transfusion of fluids such as blood. As used herein the term "graft" is used to refer to all such transplants, transfusions and grafts.

Even where tissue matching is carried out, if the donor and recipient are genetically distinct, there remains a risk that the recipient's immune system will recognise the graft and mount an immune response against it. This is commonly known as transplant rejection. It may be a particular problem where transplantation of tissues, organs or cells occurs between individuals of different species (xenotransplantation) owing to the greater genetic and consequent molecular difference between donor and recipient.

It is standard procedure to reduce risk of rejection and the severity of the resultant immune response through the use of immune suppressive drugs. These commonly act to damp down the response of the immune system, but carry with them some risk of illness, for example through a reduced ability of the transplant recipient to fight off infectious diseases or opportunistic pathogens.

The immune reaction against a graft will of course generally involve T cells. T cells which are reactive against, or recognise molecular targets derived from the graft will become activated and proliferate. Under these, or similar circumstances, an otherwise normal immune reaction (i.e. to a 'foreign' target in the body) may cause pathology as the graft is attacked. Such rejection is naturally considered to be a disease, even though in the context of the functioning of the immune system, it is a 'normal' reaction to a foreign body. Thus, undesirable cell division (proliferation of lymphocytes, such as cells which target the graft) is of key importance in the development of immune reactions against transplanted organs, tissues or cells.

A further example of an immune condition in which undesirable cell division occurs is 'Graft versus host disease' following a bone marrow transplantation (or transfusion). T cells present in the graft, either as contaminants or intentionally introduced into the host, attack the tissues of the transplant recipient after perceiving host tissues as antigenically foreign. The T cells produce an excess of cytokines, including TNFα and interferon-gamma (IFNγ). A wide range of host antigens can initiate graft-versus-host-disease, among them the human leukocyte antigens (HLAs). However, graft-versus-host disease can occur even when HLA-identical siblings are the donors.

Hypersensitivity reactions are undesirable (damaging, discomfort-producing and sometimes fatal) reactions produced by the normal immune system. Hypersensitivity reactions require a pre-sensitized (immune) host. A four-group classification was expounded by Gell and Coombs.

Therefore undesirable cell division links many conditions of ill health, such as cancer, autoimmune disease, transplant rejection and graft versus host disease. In these conditions the body's aggressive reaction (or the reaction of the transplanted T cells) may be characterised by a rapidly dividing pool of cells (e.g. activated lymphocytes). Proliferating activated lymphocytes may be considered to be hyperproliferative within the meaning of this invention. A link between all of the conditions discussed is the persistence of proliferation, especially in the face of a variety of stimuli opposed to such proliferation.

βGBP has attracted interest as a potential therapeutic agent for a number of reasons. Importantly, βGBP is a natural regulatory molecule, produced primarily by the immune system, which because of its very nature and function, will not harm normal cells. βGBP is believed to play a part in the natural mechanisms and feedback circuitries governing the regulation of immune cell proliferation. In addition, βGBP is thought to play a part in cancer prevention and surveillance constitutively.

Low concentrations of βGBP are already known to inhibit the growth of T cells in vitro (Blaser et al., 1998). It has also been disclosed that at very much higher (i.e. micromolar) concentrations homodimers formed from βGBP (a complex with lectin-like characteristics known as Galectin-1 or GAL-1) can induce rapid apoptosis in activated T cells in vitro. This property is only evident at high concentrations where GAL-1 (i.e. the dimeric molecule) forms (Rabinovich et al., 1999).

It is however important to make the distinction between the known activities of GAL-1 and βGBP. This distinction is discussed in the prior art, for example in WO 92/07938, and summarised briefly below.

GAL-1 mediates its pro-apoptotic effects through its Lectin-like properties. High concentrations of GAL-1 rapidly induce apoptosis in activated T cells. Competition with lactose inhibits the pro-apoptotic effects of GAL-1, suggesting that they are mediated through crosslinking of cell surface glycoproteins.

In contrast the growth inhibitory effects of βGBP are independent of the carbohydrate binding site (i.e. independent of GAL-1 type lectin activity). This is demonstrated by the fact that the addition of lactose does not block βGBP activity and also that the 18000 Mr murine form of βGBP, in which the carbohydrate binding site is blocked by a glycan complex, has full growth inhibitory activity. Thus βGBP monomers (which do not have lectin-like characteristics) mediate their effects via an alternative mode of action. βGBP is believed to interact with a specific cell surface receptor and induce signal transduction events.

The threshold concentration for apoptotic activity of GAL-1 has previously been shown to be 4 μg/ml (Rabinovich et al., 1999, Rabinovich et al., 1998, Rabinovich et al., 1997). It was previously shown that the dimeric molecule was necessary for the biological effects (i.e. induction of apoptosis in T cells) of GAL-1. However, the biological activities of βGBP with regard to the inhibition of cell division, rather than the induction of apoptosis, are known to be exerted at concentrations measured in the range of nanograms per ml. Thus it is possible to make a clear distinction between the known activities and properties of βGBP (cytokine-like) and GAL-1 (lectin-like).

It would be useful if there were further therapeutic options in the treatment of conditions which involve disease associated cell division. Such disease associated cell division may alternatively be considered as 'undesirable' cell division since as described above the cell division may take place as part of a breakdown of normal control (e.g. cancer or other hyperproliferative conditions), or under circumstances where the division might be regarded as 'normal' but misdirected (e.g. lymphocyte proliferation in autoimmune conditions) or 'normal' but unwanted (e.g. an immune response to a foreign tissue that is beneficial such as a transplanted organ).

It is an object of the invention to provide medicaments useful in the treatment of such conditions, or to at least provide the public and/or medical community with a useful alternative.

SUMMARY OF THE INVENTION

Where a term is defined or discussed herein that definition or discussion is intended to apply to all uses and instances of the term, unless otherwise stated.

The present invention makes use of the properties of βGBP. In particular it is based around the effect of βGBP on cells which either (i) do not respond at all to the growth inhibitory effects of βGBP (i.e. they will not be susceptible to arrest of the cell cycle by βGBP) or (ii) have been subjected to a mitogentic stimulus. Stimulation may be such that their proliferation, or ability to proliferate is encouraged or enhanced. Both types of cells may be considered to be hyper proliferative cells. Examples of the former type are cancer cells which have developed to the stage that they no longer respond to the growth inhibitory effects of βGBP. Such cancer cells can be regarded as 'aggressive' or 'invasive' cells. Examples of the latter type are cancer cells which retain some sensitivity to the growth inhibitory effects (e.g. when not mitogenically stimulated) of βGBP, the mitogentic stimulation acts to mimic in the latter cell type the behaviour and characteristics of the former.

The term 'aggressive' may also be applied for example to lymphocytes which have been activated and are dividing. Such lymphocytes may continue to divide persistently and may be considered to be persistently dividing cells. Such persistent behaviour may apply in particular to lymphocytes such as T cells which are responding to the presence of 'antigenically foreign' grafts (e.g. transplant rejection) or cells that are participating in an autoimmune condition.

Any cell which continues to divide in the face of negative regulatory signals/conditions, stimuli or drugs may be considered to be a persistently dividing cell. The term "invasive" is often used in a clinical setting to describe the behaviour of cancer cells which are persistently dividing and infiltrating other adjacent tissues or metastasizing to different locations.

In particular, the present invention is related to the discovery that proliferative stimuli (e.g. pro-mitogenic stimuli) in conjunction with βGBP can induce apoptosis. Thus the combination of a mitogenic stimulus together with βGBP may induce apoptosis in cells which would not normally respond to βGBP with apoptosis. In addition, these properties of βGBP can be applied in the context of other cells which may be considered to be hyperproliferative, such as lymphocytes and in particular T cells, which are activated and proliferating as part in a disease associated, or undesirable, immune reaction.

The term "hyperproliferative condition" is used to encompass any condition characterised by excessive cell growth (or insufficient apoptosis). Examples of hyperproliferative conditions are cancer and inappropriate or undesirable immune responses as discussed above.

Thus mitogenic stimulation, in conjunction with βGBP can be used to promote apoptosis in hyperproliferative cells such as cancer cells, or activated and persistently dividing lymphocytes. Mitogenic stimulation of cells (including those cancer cells which are considered less aggressive, and which may still retain some sensitivity to the growth inhibitory effects of βGBP) enhances the pro-apoptopic function of βGBP on said cells. Mitogenic stimulation may thus be considered to convert a less aggressive cell into a cell which is then more susceptible to the induction of apoptosis by βGBP. Similarly stimulation and activation of lymphocytes such as T cells renders them more susceptible to the induction of apoptosis by βGBP.

Accordingly, in a first aspect the present invention provides use of βGBP in the manufacture of a medicament for the prevention or treatment of a condition in which disease-associated cell division occurs, wherein the cells which result from said disease associated cell division comprise a cell in respect of which the effect of βGBP is not inhibition of growth, or wherein the cells which result from said disease associated cell division are mitogenically stimulated. The mitogenic stimulation may be such that the cell's ability to proliferate is enhanced.

By "treatment" it is meant at least improvement, preferably cure of the condition in question. Treatment may also include prophylactic, i.e. preventative treatment aimed at preventing the occurrence or severity of the condition in a subject judged to be at risk of developing a condition to be treated.

In a preferred embodiment the condition is cancer, an immune condition, or an inflammatory condition.

The term "cancer" is intended to be interpreted broadly and may encompass any neoplasm, either benign or malignant. Cancer may be of epithelial or mesenchymal origin. As used herein, the term cancer may therefore refer to a neoplasm derived from any cell type or of any severity. Thus, for example, the term cancer may refer to a carcinoma, lymphoma or leukaemia, sarcoma, mesothelioma, glioma, germinoma or choriocarcinoma. Examples of specific types of cancer for which the uses, medicaments, pharmaceutical compounds and methods of the present invention may be useful include breast cancer, colon cancer, ovarian cancer, oral cancer, prostate cancer, stomach cancer leukaemia, lung cancer, testicular cancer, liver cancer, pancreatic cancer, lipoma, sarcoma or others. It is envisaged that any cancer is potentially treatable according to the invention.

By "leukaemia" it is meant any cancer of the blood or bone marrow. It is intended to cover acute, chronic, lymphoid and myeloid forms for leukaemia. For example, acute lyphocytic leukaemia (ALL), acute myelogenous leukaemia (also known as acute myeloid leukaemia, or AML), chronic lymphocytic leukaemia (CLL) and chronic myelogenous leukaemia (CML) are all intended to be covered by the definition of leukaemia.

An example of a cell in respect of which the effect of βGBP is not inhibition of growth is one that may be characterised by high-ERK levels, fast proliferation rates, and high levels of akt gene expression and active (i.e. phosphorlyated) Akt protein, when compared to a control cell. Cells that over express ErbB2 are examples of such cells. In these cells βGBP is unable to overcome the force of mitogenic signalling. However, as described herein βGBP promptly reduces akt gene expression with consequent loss of Akt protein, thereby abolishing the cancer cells survival signalling. Thus βGBP induced loss of akt gene expression is followed (after two or three replication cycles) by massive cell death owing to induced apoptosis.

The person skilled in the art would as a matter of routine be able to determine whether a cancer comprised a cell on which the effect of βGBP is not inhibition of growth. Methods of analysing the character and behaviour of cancer cells, either in the body, or in a sample which has been removed from the body, are well known to those skilled in the art. For example such methods may comprise the removal of a sample from the body and study of cells from the sample directly or in culture. Such cells can easily be contacted with βGBP or other test substances or compounds and the subsequent effect on the cells determined.

The medicaments of the invention may be formulated for any suitable dosage regimen. In further preferred embodiments the cancer is colon cancer and a single dose of βGBP is sufficient to achieve a concentration in the subject of 15-150 µg/kg. In particularly preferred embodiments wherein the cancer is colon cancer, a single dose of βGBP is sufficient to achieve a concentration in the subject of 15-60 µg/kg. Alternatively, doses of 50, 40, 30, 20, 10 or 5 µg/kg may be useful. Lower concentrations or doses may be preferred for economic reasons, for convenience of administration and other reasons.

βGBP may be used at a range of doses or concentrations which could be determined by the person skilled in the art from the data presented herein. For example in some instances βGBP may be used at concentrations of 0.1, 0.5, 1, 2, 3.5, 5, 7, 10, 15, 20, 30, 35, 40, or 50 nM. Other concentrations may be possible.

In an alternative preferred embodiment the condition is an immune condition and the immune condition is an autoimmune condition, is an alloimmune condition, comprises an immune reaction to a graft, comprises an immune reaction by a graft, comprises a hypersensitivity reaction, or comprises the persistent proliferation of activated lymphocytes.

In such embodiments, use of the medicament to treat an individual may be capable of bringing about immune tolerance, or a condition comparable to immune tolerance in that individual in the context of the immune reaction of interest. Similarly tolerance may be achieved owing to the products, pharmaceutical compounds, uses or methods which form part of the present invention.

In preferred embodiments the cells which result from said disease associated cell division comprise a cell which has a high intrinsic mitogenic capacity, is mitogenically stimulated, is a rapidly dividing cell, or is a persistently dividing cell.

By "high intrinsic mitogenic capacity" it is meant that the cell in question is capable of dividing more rapidly than would be expected for a control cell. Similarly a "rapidly dividing cell" is one which divides more rapidly than would be anticipated for a control cell of the same type. "A persistently dividing cell" is one which continues to divide despite the presence of stimuli that discourage cell division and growth. Such stimuli may include normal physiological stimuli on an intrinsic genetic level, or from autocrine or paracrine effects from self tissue derived sources, or other normal physiological signals employed by the body. Other such stimuli may include exogenously provided factors such as drugs which aim to prevent cell division.

It is not possible to define such cells in empirical terms since cell division rates will vary between cell types (e.g. tissue types) and for cells of the same type which are growing under different conditions. Thus, it is only possible to talk of cell division rates and mitogenic capacities in relative terms.

The skilled person is of course capable of assessing what would be expected for a cell of a given type in terms of mitogenic capacity, rapidity or persistence of cell division. The skilled person could for example compare 'normal' (i.e. not disease associated, or unstimulated cells) with cells taken from, for example, a biopsy from a tumour or a clone of lymphocytes involved in disease. Such assessments might be made in situ, in vitro, ex vivo, or in an experimental animal.

In other preferred embodiments the cells which result from said disease associated cell division comprise a cell which is or is suspected of being a hyperproliferative cell, a neoplastic cell, a cancer cell, an activated lymphocyte, an activated T cell, an activated B cell, a persistently dividing lymphocyte, an activated inflammatory cell, or an activated endothelial cell.

In further preferred embodiments the prevention or treatment of the condition comprises the administration or co-administration of a mitogen or the medicament further comprises a mitogen or is for co-administration with a mitogen.

Mitogens are agents which act on cells to encourage cell division. In the present invention, a mitogen is any molecule which acts to exert a mitogenic (i.e. proliferative) effect on a cell. Suitable mitogens for use in the present invention would be known to those skilled in the art and include hormones such as estrogens, androgens and related molecules, growth factors and antigenic determinants which bind to receptors on lymphocytes.

Antigenic determinants are also sometimes known as antigens (although this term is more normally used in a broader less specific sense), cognate antigens, or epitopes. Such antigenic determinants are commonly peptides, but may also include other molecules such as carbohydrates or nucleic acids. The term antigenic determinant in this context is intended to encompass specific molecules which bind to the appropriate lymphocyte receptor, or larger molecules, or even whole proteins or cells which comprise said antigenic determinants.

Antigenic determinants appropriate for use in the present invention may correspond to those responsible for an autoimmune reaction, responsible for an alloimmune reaction, be derived from a transplant, graft or transfusion, be derived from an allergen, or be capable of stimulating the proliferation of activated lymphocytes.

Other known mitogens include for example, cytokines, toxins (such as cholera toxin B) and other molecules from diverse sources including Lysophosphatidic acid (LPA), phytohaemagglutinin, concanavalin A, Lipopolysaccharide (LPS) and pokeweed mitogen. Not all mitogens may be suitable in all circumstances. Therapeutically relevant mitogens would be clear to the skilled person. Other mitogens may be useful in an in vitro context or experimentally.

Mitogenic stimulation may alternatively be via genetic means. For example mutation, or transfection with suitable genetic elements including those coding for mutated forms of signal transduction proteins such as Ras.

Certain molecules exert a mitogenic effect only on certain cell types. For example an estrogen would be expected to have a mitogenic effect on mammary tissue cells, such as breast cancer cells. Conversely, androgens would be expected to have a mitogenic effect on, for example prostate cells such as prostate cancer cells. In particular a mitogentic effect is observed where the hormone receptor is overexpressed. Estrogens and androgens would not be expected to be mitogentic for all cell types.

Thus in some cases, the type of cell concerned will influence what compounds may be considered to be mitogens. The skilled person would know whether a given compound has a mitogenic activity with respect to a given cell type. However, it would be merely a matter of routine experimentation for the skilled person to assess the effect on cell growth of a given compound. For example, an individual, or a sample comprising a cell may be treated with a putative mitogen. The effect on cell growth may then be assessed. Suitable methods for assessing cell growth are disclosed herein and include, for example direct hemocytometer counting, flow cytometry and measurement of the incorporation of labelled molecules such as nucleotides into growing cells.

In preferred embodiments the mitogen is a hormone, a growth factor, or an antigenic determinant which binds to a receptor on a lymphocyte.

In particularly preferred embodiments the hormone is an estrogen or an androgen.

By "an estrogen" (alternative spelling oestrogen) it is meant any one of the group of steroid hormones commonly referred to as estrogens, and also analogs and derivatives that possess estrogenic activity.

Examples of naturally occurring estrogens are estriadiol, estriol and estrone, which are produced under normal circumstances in the body through the action of enzymes on androgens. An example of an estriadiol is 17β-estriadiol (the primary estrogen in pre-menopausal women).

The term estrogen as used in the context of the present invention also encompasses natural and synthetic substances that also possess estrogenic activity. Examples of natural substances with such activity are phytoestrogens derived from plants such as soya beans. Synthetic estrogen analogs and estrogen derivatives, such as those used in hormone based (e.g. oral) contraceptives, may also be used. An example is ethinylestradiol. Further synthetic substances with estrogenic activity may also be referred to as xenoestrogens.

In yet other preferred embodiments the mitogen is a growth factor which binds a tyrosine kinase receptor. Examples of such growth factors are PDGF, EGF, FGF, or IGF.

Alternatively, the mitogen is a growth factor which binds a G protein coupled receptor. Examples of such growth factors are vasopressin, bombesin, thrombospondin, or bradykinin.

In other preferred embodiments the mitogen is an antigenic determinant which binds to a receptor on a lymphocyte and the receptor is a T cell receptor (TCR), an antibody, or an MHC molecule.

In preferred embodiments the medicament promotes apoptosis of the cells which result from said disease associated cell division.

By "promotes apoptosis" or "the promotion of apoptosis" it is meant that the effect of βGBP is to increase the likelihood of apoptosis in a cell. For example, contacting the cell with βGBP brings about changes in the cell which favour apoptosis rather than survival. The skilled person could assess this in a straightforward manner. For example by comparing a statistically significant number of cells over an appropriate time course (for example several days) and observing whether the addition of βGBP gave rise to an increase in apoptosis in comparison with the rate observed for control cells.

Suitable methods for assessing apoptosis are well known in the art and examples are described elsewhere herein. These include Tetramathylrhodamine ethyl ester staining, plasma membrane phosphatidyly serine analysis, caspase 3 activity assessment and TUNEL analysis.

In the context of the present invention an individual or subject may be any animal, preferably a mammal and most preferably a human.

In another aspect the present invention provides use of a mitogen in the manufacture of a medicament for the prevention or treatment of a condition in which disease-associated cell division occurs, wherein the cells which result from said disease associated cell division comprise a cell in respect of which the effect of βGBP is not inhibition of growth, or wherein the cells which result from said disease associated cell division are mitogenically stimulated, and wherein the prevention or treatment of the condition comprises the administration or co-administration of a βGBP, or the medicament further comprises a βGBP or is for co-administration with a βGBP.

The mitogenic stimulation may be such that the cell's ability to proliferate is enhanced.

In preferred embodiments the condition is cancer, an immune condition, or an inflammatory condition.

In preferred embodiments the condition is cancer and the cancer is colon cancer, and a single dose of the medicament or coadministered βGBP is sufficient to achieve a concentration of βGBP in the subject of 15-150 μg/kg.

In a particularly preferred embodiment the condition is cancer, the cancer is colon cancer, and a single dose of the medicament or coadministered βGBP is sufficient to achieve a concentration of βGBP in the subject of 15-60 μg/kg.

In alternative preferred embodiments the condition is an immune condition and the immune condition is an autoimmune condition, is an alloimmune condition, comprises an immune reaction to a graft, comprises an immune reaction by a graft, comprises a hypersensitivity reaction, or comprises the persistent proliferation of activated lymphocytes.

In preferred embodiments the cells which result from said disease associated cell division comprise a cell which has a high intrinsic mitogenic capacity, is mitogenically stimulated, is a rapidly dividing cell, or is a persistently dividing cell.

In preferred embodiments the cells which result from said disease associated cell division comprise a cell which is or is suspected of being a hyperproliferative cell, a neoplastic cell, a cancer cell, an activated lymphocyte, an activated T cell, an activated B cell, a persistently dividing lymphocyte, an activated inflammatory cell, an activated endothelial cell.

In preferred embodiments the mitogen is a hormone, is a growth factor, is or comprises an antigenic determinant which binds to a receptor on a immune cell.

In particularly preferred embodiments the mitogen is a hormone and the hormone is an estrogen or an androgen, a growth factor which binds a tyrosine kinase receptor, a growth factor which binds a G protein coupled receptor, or an antigenic determinant which binds to a receptor on a immune cell and wherein the receptor is a T cell receptor (TCR), an antibody, or an MHC molecule.

In preferred embodiments the medicament promotes apoptosis of the cells which result from said disease associated cell division.

In another aspect the invention provides βGBP for use in the prevention or treatment of a condition in which disease-associated cell division occurs, wherein the cells which result from said disease associated cell division comprise a cell in respect of which the effect of βGBP is not inhibition of growth, or wherein the cells which result from said disease associated cell division are mitogenically stimulated.

The mitogenic stimulation may be such that the cell's ability to proliferate is enhanced.

In preferred embodiments the condition is cancer, an immune condition, or an inflammatory condition.

In preferred embodiments the condition is cancer, the cancer is colon cancer, and a single dose of βGBP is sufficient to achieve a concentration in the subject of 15-150 μg/kg.

In a particularly preferred embodiment the condition is cancer, the cancer is colon cancer, and a single dose of βGBP is sufficient to achieve a concentration in the subject 15-60 μg/kg.

In alternative preferred embodiments the condition is an immune condition and the immune condition is an autoimmune condition, is an alloimmune condition, comprises an immune reaction to a graft, comprises an immune reaction by a graft, comprises a hypersensitivity reaction, or comprises the persistent proliferation of activated lymphocytes.

In preferred embodiments the cells which result from said disease associated cell division comprise a cell which has a high intrinsic mitogenic capacity, is mitogenically stimulated, is a rapidly dividing cell, or is a persistently dividing cell.

In preferred embodiments the cells which result from said disease associated cell division comprise a cell which is or is suspected of being a hyperproliferative cell, a neoplastic cell, a cancer cell, an activated lymphocyte, an activated T cell, an activated B cell, a persistently dividing lymphocyte, an activated inflammatory cell, or an activated endothelial cell.

In preferred embodiments the prevention or treatment of the condition comprises the administration or co-administration of a mitogen, or the medicament further comprises a mitogen or is for co-administration with a mitogen.

In preferred embodiments the mitogen is a hormone, is a growth factor, or is or comprises an antigenic determinant which binds to a receptor on a immune cell.

In preferred embodiments the mitogen is a hormone and the hormone is an estrogen or an androgen, a growth factor which binds a tyrosine kinase receptor, a growth factor which binds a G protein coupled receptor, or an antigenic determinant which binds to a receptor on a immune cell and wherein the receptor is a T cell receptor (TCR), an antibody, or an MHC molecule.

In preferred embodiments the medicament promotes apoptosis of the cells which result from said disease associated cell division.

In another aspect the invention provides a mitogen for use in the prevention or treatment of a condition in which disease-associated cell division occurs, wherein the cells which result from said disease associated cell division comprise a cell in respect of which the effect of βGBP is not inhibition of growth, or wherein the cells which result from said disease associated cell division are mitogenically stimulated, and the prevention or treatment of the condition comprises the administration or co-administration of βGBP, or the medicament further comprises βGBP or is for co-administration with βGBP.

The mitogenic stimulation may be such that the cell's ability to proliferate is enhanced.

In preferred embodiments the condition is cancer, an immune condition, or an inflammatory condition.

In preferred embodiments the condition is cancer, the cancer is colon cancer, and a single dose of the medicament or coadministered βGBP is sufficient to achieve a concentration of βGBP in the subject of 15-150 μg/kg.

In a particularly preferred embodiment the condition is cancer, the cancer is colon cancer, and a single dose of the medicament or coadministered βGBP is sufficient to achieve a concentration of βGBP in the subject of 15-60 μg/kg.

In alternative preferred embodiments condition is an immune condition and the immune condition is an autoimmune condition, is an alloimmune condition, comprises an immune reaction to a graft, comprises an immune reaction by a graft, comprises a hypersensitivity reaction, or comprises the persistent proliferation of activated lymphocytes.

In preferred embodiments the cells which result from said disease associated cell division comprise a cell which has a high intrinsic mitogenic capacity, is mitogenically stimulated, is a rapidly dividing cell, or is a persistently dividing cell.

In preferred embodiments the cells which result from said disease associated cell division comprise a cell which is or is suspected of being a hyperproliferative cell, a neoplastic cell, a cancer cell, an activated lymphocyte, an activated T cell, an activated B cell, a persistently dividing lymphocyte, an activated inflammatory cell, or an activated endothelial cell.

In preferred embodiments the mitogen is a hormone, is a growth factor, or is or comprises an antigenic determinant which binds to a receptor on a immune cell.

In preferred embodiments the mitogen is a hormone and the hormone is an estrogen or an androgen, a growth factor which binds a tyrosine kinase receptor, a growth factor which binds a G protein coupled receptor, or an antigenic determinant which binds to a receptor on a immune cell and wherein the receptor is a T cell receptor (TCR), an antibody, or an MHC molecule.

In preferred embodiments the medicament promotes apoptosis of the cells which result from said disease associated cell division.

The present invention further provides a product containing βGBP and a mitogen for simultaneous, separate or sequential use in the treatment of a condition in which disease associated cell division occurs, wherein the cells which result from said disease associated cell division comprise a cell in respect of which the effect of βGBP is not inhibition of growth, or wherein the cells which result from said disease associated cell division are mitogenically stimulated The mitogenic simulation may be such that the cells ability to proliferate is enhanced.

In preferred embodiments the condition is cancer, an immune condition, or an inflammatory condition.

In preferred embodiments the mitogen is a hormone, a growth factor, or is or comprises an antigenic determinant which binds to a receptor on an immune cell.

In preferred embodiments the mitogen is a hormone and the hormone is an estrogen or an androgen, a growth factor which binds a tyrosine kinase receptor, a growth factor which binds a G protein coupled receptor, or an antigenic determinant which binds to a receptor on a immune cell and wherein the receptor is a T cell receptor (TCR), an antibody, or an MHC molecule.

In a further aspect the invention provides a pharmaceutical composition comprising a therapeutically effective amount of βGBP and a therapeutically effective amount of mitogen.

By "therapeutically effective amount" is meant an amount of the compound (e.g. βGBP and/or a mitogen) sufficient to give rise to the desired therapeutic effect. For example, the therapeutically effective amount is an amount sufficient to treat or prevent cancer.

In preferred embodiments the mitogen is a hormone, a growth factor, or is or comprises an antigenic determinant which binds to a receptor on a lymphocyte.

In preferred embodiments the mitogen is a hormone and the hormone is an estrogen, an androgen, a growth factor which binds a tyrosine kinase receptor, a growth factor which binds a G protein coupled receptor, or an antigenic determinant which binds to a receptor on a immune cell and wherein the receptor is a T cell receptor (TCR), an antibody, or an MHC molecule.

In preferred embodiments the composition is formulated in individual unit dose form, and wherein a single dose of the medicament is sufficient to achieve a concentration in the subject of 15-150 µg/kg.

In a particularly preferred embodiment the composition is formulated in individual unit dose form, and wherein a single dose of the medicament is sufficient to achieve a concentration in the subject of 15-60 µg/kg.

Such a dose of βGBP may be particularly preferred when the pharmaceutical composition is suitable for use in the treatment of cancer and in particular where the cancer is colon cancer.

The medicaments, products and pharmaceutical compositions of the invention may contain any number of pharmaceutically acceptable excipients. Those excipients used in the art are generally well known and they include fillers, lubricants, colours, flavours, wetting agents, solvents, buffering agents, preservatives and the like.

The medicaments, products and pharmaceutical compositions of the invention may be delivered or administered by any suitable route. Typically, these routes of administration would include intravenous, intraperitoneal, subcutaneous, intrathecal, intraventricular, or topical delivery. Alternatively, oral, rectal or vaginal delivery may be appropriate. Administration may also be local or systemic.

In a yet further aspect the present invention provides use of βGBP to inhibit PI3 Kinase enzyme activity, comprising contacting a cell with βGBP.

Inhibition of PI3K may be by any amount. In particular, the activity of the enzyme as compared to control cells may be reduced by 5%, 10%, 15%, 20%, 25%, 30%, 35%, 40%, 45%, 50% or more. This may be assessed for example by direct measurement of PI3K activity or from assessments of total cell PIP3 (the product of PIK3 activity).

Also provided is use of βGBP to inhibit the expression of akt, comprising contacting a cell with βGBP.

By reducing expression it is meant that the levels or quantities of akt, A mRNA and/or protein are reduced in cells that have been contacted with βGBP when compared to untreated cells. A reduction in the mRNA levels may be accompanied by an equivalent reduction in protein levels. Alternatively, the protein levels may be reduced to a different degree, e.g. a lesser reduction, or no reduction in protein levels. The extent to which the levels of mRNA or protein are reduced may vary. Levels may be reduced for example by 25%, 50%, 65%, 75%, 80%, 85%, 90%, 95%, 97%, 98%, 99% or more when compared to the levels observed for control cells. Alternatively, the reduction in the level of mRNA or protein may be to an undetectable level (i.e. apparently a reduction by 100%) using a specified detection method, such as for example Northern or Western blotting. The reduction in levels of mRNA or protein may be such that said expression may be regarded as silenced by βGBP according to the invention.

In preferred embodiments the effect of βGBP on said cell is not inhibition of growth.

In preferred embodiments the use is in vitro, in vivo, or on a sample which has been removed from the body, wherein the sample comprises a cell and which sample, or a portion thereof, is subsequently returned to the body.

In preferred embodiments the effect of contacting said cell with βGBP is the promotion of apoptosis.

In a further aspect the present invention provides a method of inhibiting PI3 Kinase, comprising contacting a cell with βGBP, whereby said method inhibits PI3 Kinase.

In a further aspect the invention provides a method of reducing the expression of akt in a cell, comprising contacting said cell with βGBP, whereby the expression of akt is reduced.

In another aspect the invention provides a method of promoting apoptosis in a cell comprising contacting said cell with βGBP, whereby apoptosis is promoted.

In yet another aspect the invention provides a method of treating or preventing a condition in which disease-associated cell division occurs, wherein the cells which result from said disease associated cell division comprise a cell in respect of which the effect of βGBP is not inhibition of growth, or wherein the cells which result from said disease associated cell division are mitogenically stimulated, whereby the condition is treated or prevented.

The mitogenic stimulation may be such that the cells ability to proliferate is enhanced.

In preferred embodiments the condition is cancer, an immune condition, or an inflammatory condition.

In preferred embodiments the condition is cancer, the cancer is colon cancer, and the method comprises achieving a concentration in the subject of 15-150 µg/kg.

In a particularly preferred embodiment the condition is cancer, the cancer is colon cancer, and the method comprises achieving a concentration in the subject 15-60 µg/kg.

In alternative preferred embodiments the condition is an immune condition and the immune condition is an autoimmune condition, is an alloimmune condition, comprises an immune reaction to a graft, comprises an immune reaction by a graft, comprises a hypersensitivity reaction, or comprises the persistent proliferation of activated lymphocytes.

In preferred embodiments the cells which result from said disease associated cell division comprise a cell which has a high intrinsic mitogenic capacity, is mitogenically stimulated, is a rapidly dividing cell, or is a persistently dividing cell.

In preferred embodiments the cells which result from said disease associated cell division comprise a cell which is or is suspected of being a hyperproliferative cell, a neoplastic cell, a cancer cell, an activated lymphocyte, an activated T cell, an activated B cell, a persistently dividing lymphocyte, an activated inflammatory cell, or an activated endothelial cell.

In preferred embodiments the method comprises mitogenic stimulation by contacting the cell with a mitogen.

In preferred embodiments the mitogen is a hormone, is a growth factor, or is or comprises an antigenic determinant which binds to a receptor on a immune cell.

In preferred embodiments the mitogen is a hormone and the hormone is an estrogen or an androgen, a growth factor which binds a tyrosine kinase receptor, a growth factor which binds a G protein coupled receptor, or an antigenic determinant which binds to a receptor on a immune cell and wherein the receptor is a T cell receptor (TCR), an antibody, or an MHC molecule.

In preferred embodiments the method promotes apoptosis of the cells which result from said disease associated cell division.

The effect of βGBP on the cell may not be the inhibition of growth.

In yet a further aspect the invention provides a method of assessing the suitability of βGBP as a therapeutic agent comprising, contacting a sample obtained from a subject with βGBP, said sample comprising a cell, and determining whether contact with βGBP has a pro-apoptotic effect on said cell, wherein, if a pro-apoptotic effect is observed, then treatment of the subject with βGBP is expected to result in apoptosis.

Apoptosis would then be expected to occur in cells which were equivalent to, or similar to the cells of the sample. Thus if apoptosis were observed in the sample then βGBP may be considered to be a suitable pro-apoptotic therapeutic agent for example. If apoptosis is only observed in the sample when further mitogenic stimulation is provided then βGBP might be considered to be suitable only for arresting cell growth rather than inducing apoptosis. Alternatively, if the induction of apoptosis was preferred then the administration of βGBP along with suitable mitogenic stimulation would be indicated.

In preferred embodiments the cell is, or is suspected of being a hyperproliferative cell, a neoplastic cell, a cancer cell, an activated lymphocyte, an activated T cell, an activated B cell, a persistently dividing lymphocyte, an activated inflammatory cell, or an activated endothelial cell.

In preferred embodiments said cell has a high intrinsic mitogenic capacity, is mitogenically stimulated, is a rapidly dividing cell, or is a persistently dividing cell.

In preferred embodiments the method further comprises mitogenic stimulation of said cell.

In preferred embodiments the mitogenic stimulation comprises contacting the cell with a hormone, a growth factor, or an antigenic determinant which binds to a receptor on a lymphocyte.

In preferred embodiments the mitogen is a hormone and the hormone is an estrogen, an androgen, a growth factor which binds a tyrosine kinase receptor, a growth factor which binds a G protein coupled receptor, or an antigenic determinant which binds to a receptor on a immune cell and wherein the receptor is a T cell receptor (TCR), an antibody, or an MHC molecule.

The methods of the invention may be carried out in vitro, in vivo, or on a sample which has been removed from the body, wherein the sample comprises a cell and which sample, or a portion thereof, is subsequently returned to the body.

In the uses and methods described above reference is made to transformed cells, immortalised cells and neoplastic cells. An "immortalised cell" is one which has acquired the ability to proliferate indefinitely either through random mutation or deliberate modification. Cells may be immortalised by the artificial expression of the telomerase gene for example, or may be spontaneously immortalised by random mutations (e.g. acquired in cell culture). A "neoplastic cell" is a cell derived from a neoplasm. Reference is made to the discussion of neoplasm and cancer above.

It is envisaged that the compounds, methods and uses of the invention may find application in an in vitro or in vivo context. Further applications are envisaged on samples which have been removed from the body (sometimes described as ex vivo samples) as discussed above.

Thus the invention may also be used in the context of transformed cells. By a "transformed cell" it is meant a cell which has been modified by the introduction of exogenous DNA or RNA.

It will be appreciated that the teaching of the invention applies to whole organisms and individual cells of said organisms either in situ or when removed from the body and maintained in culture for a period of time. Samples, or portions of samples which may comprise cultured cells may be returned to the organism after having been removed.

Alternatively, the teaching of the present invention may be applied to cell lines grown in culture. Such cultured cell lines may be of any sort known to one skilled in the art, for example primary cell cultures or stable cell lines, optionally comprising further modifications. Cultured cell lines may include specific cancer cell lines. Specific reference is made to the cell lines discussed below in the Examples.

The teaching of the present invention relates to therapeutic and non-therapeutic scenarios. It may also be applied in cosmetic context.

BRIEF DESCRIPTION OF THE FIGURES

FIG. 2 shows the changes in mitogenic input in non cancerous cells and response to treatment with Hu-r-βGBP. In all panels Hu-r-βGBP was added at hour 3 after seeding.

FIG. 4 illustrates a proposed model of functional links between ERK, akt gene, PI3K and ☐GBP. The inventors do not wish to be bound by theory in this regard.

FIG. 5 shows the response of MCF-7 cells to raised mitogenic input and to treatment with Hu-r-βGBP.

DESCRIPTION OF THE INVENTION

It has surprisingly been found that βGBP inhibits PI3K activity and reduces expression of the akt gene. Unexpectedly, aggressive cancer cells that are treated with βGBP undergo delayed, massive apoptosis after 2-3 rounds of cell division, in response to the early event of reduction in akt mRNA levels. Similarly, βGBP induces apoptosis in activated persistently dividing lymphocytes such as T cells, whilst sparing naïve cells. Interestingly, increasing the mitogenic character of: normal-like cells (to create artificially aggressive or hyperproliferative cells); cancer cells of a less aggressive type; or lymphocytes such as activated T cells, renders such cells more susceptible to apoptosis induced by βGBP. Equivalent results are seen in colon cancer cells, but at much lower doses than for other cancer types.

Apoptosis: Correlation Between PI3K Inhibition and akt Gene Silencing

To determine whether βGBP could overcome the strength of endogenous mitogenic signalling in aggressive cancers, BT474 and SKBR3 breast cancer cells which express high levels of ErbB2 (Hynes et al., 1989) were examined. It was found that βGBP had virtually no effect on cell replication until, after 2-3 generation cycles, abrupt cell death was triggered by an acute sequence of apoptotic events documented by changes in mitochondrial membrane potential, functional alteration of the plasma membrane, caspase 3 activation and DNA fragmentation (FIG. 1A-D). There were no changes in ERK phosphorylation while cell replication continued unaffected, but it was observed that loss of phosphorylated Akt, and loss of Akt protein, had preceded the apoptotic process (FIGS. 1G and J).

In order to determine whether the loss of the Akt protein could be attributed to transcriptional or post-transcriptional events akt mRNA levels were assessed. FIGS. 1F and I shows that within one day from the addition of βGBP akt mRNA had become virtually undetectable. It is reasoned that, while the loss of phosphorylated Akt may point to loss of PI3K activity and Akt recruitment as one conceivable explanation, the loss of akt mRNA does not, unless PI3K activity is required for akt gene expression and unless βGBP can inhibit PI3K activity.

As cells' phosphoinositide levels do not directly represent the functional state of the PI3K enzyme, but are the result of PI3K and PTEN activity, in order to directly assess its functional state, class IA PI3K was isolated by immunoprecipitation using an antibody to the p85α adapter subunit and the ability of the co-precipitated p 110 catalytic subunit (Vanhaesenbroeck et al., 2001) to convert a standard phosphatidylinositol (4,5)P2 (PIP2) to phosphatidylinositol (3,4,5)P3 (PIP3) was assessed in a kinase reaction by measuring the generated PIP3 in a competitive ELISA.

Figure 1A:
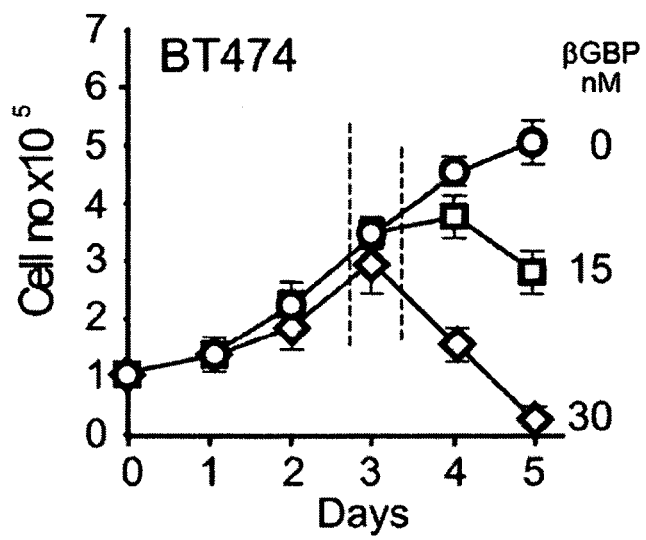
(FIGS. 1A and C) The rate of cell proliferation and cell response to Hu-r-☐GBP. Dotted lines in growth curves define the time of occurrence of apoptotic events. Values are means of triplicate cultures +/−SEM.
Figure 1B:
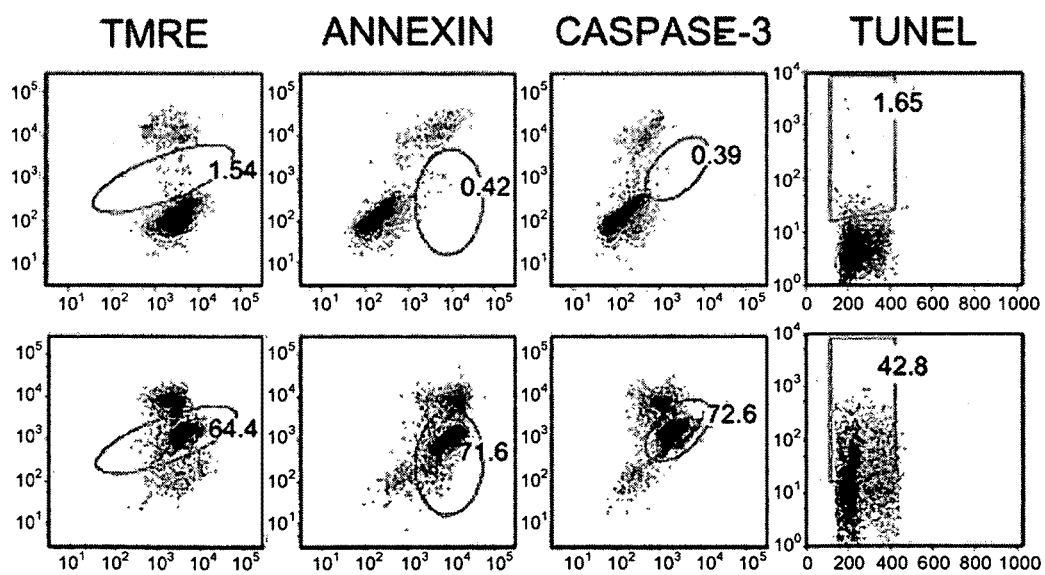
(FIGS. 1B and D) Sequential expression of apoptotic events after treatment with 30 nM Hu-r-βGBP. Left to right: loss of mitochondrial membrane potential assessed by tetramethylrhodamine ethyl ester (TMRE); phosphatidylserine orientation at the plasma membrane assessed by Annexin V staining; caspase 3 activity and DNA fragmentation (TUNEL). Apoptotic cells in circled areas. Values are percentages of cells in apoptosis. Upper panels: controls; lower panels: cells treated with 30 nM Hu-r-βGBP.
Figure 1C:
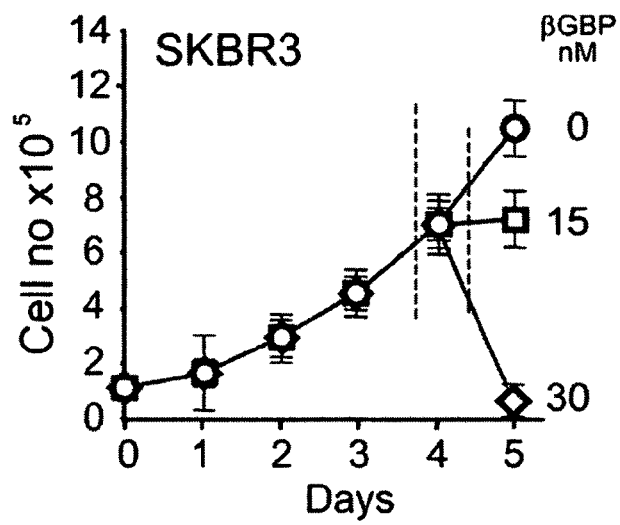
FIG. 1 shows the events leading to apoptotic death in cells overexpressing ErbB2 treated with Hu-r-βGBP. In all panels Hu-r-☐GBP was added at hour 3 after seeding.
(FIGS. 1E and H) Inhibition of class IA PI3K activity by 30 nM Hu-r-☐GBP measured as PI(3,4,5)P3 generated from immunoprecipitated PI3K in a kinase assay and assessed in a competitive ELISA. Values are means from triplicate readings +/−SEM. (F and I) akt mRNA and GAPDH mRNA levels. Left panels: controls; right panels: cells treated with 30 nM Hu-r-☐GBP.
(FIGS. 1G and J) Phosphorylated (Ser 473) Akt and total Akt protein. Left panels: controls; right panels: cells treated with 30 nM Hu-r-βGBP.
Figure 1D:
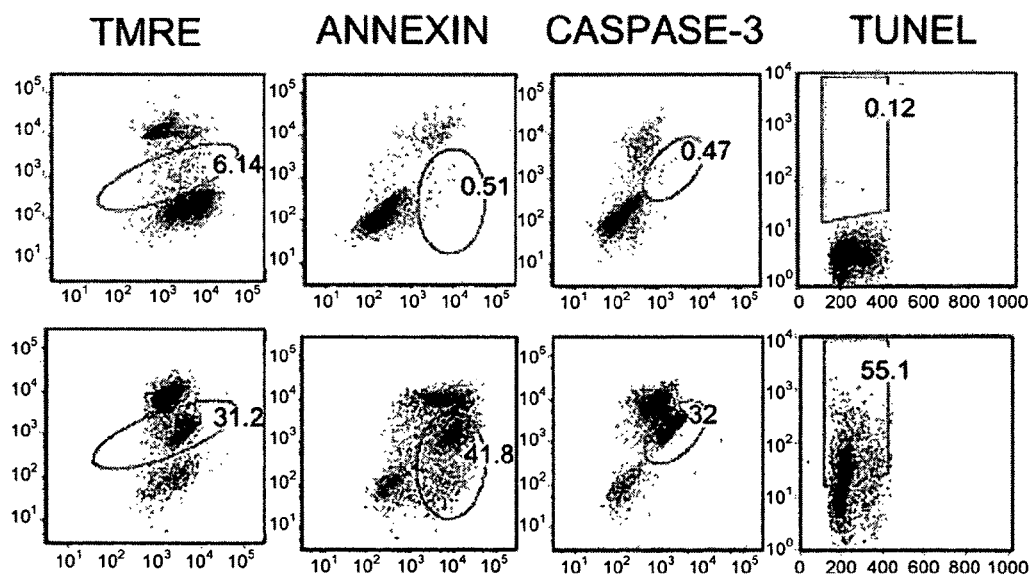
Figure 1E:
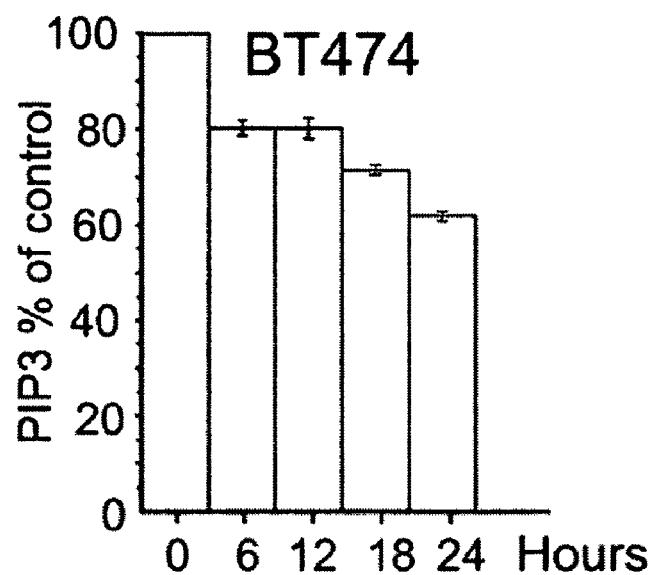
Figure 1F:
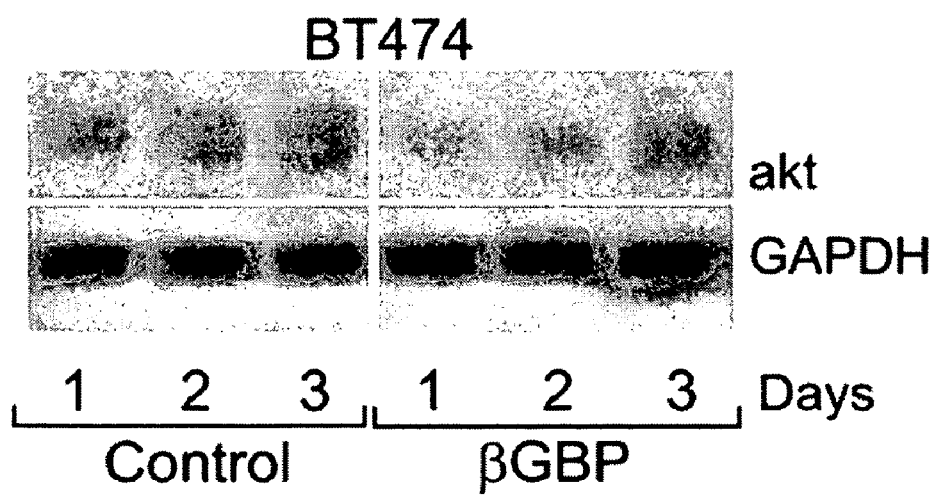
Figure 1G:
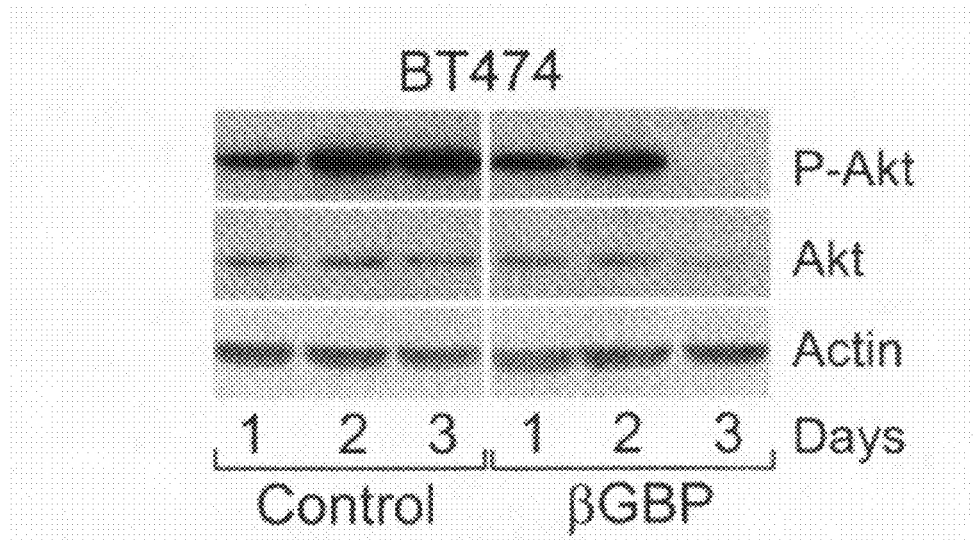
Figure 1H:
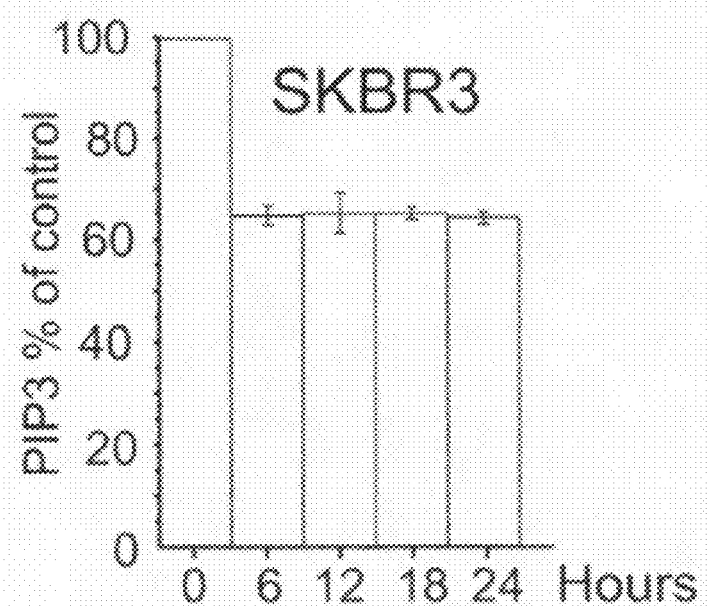
Figure 1I:
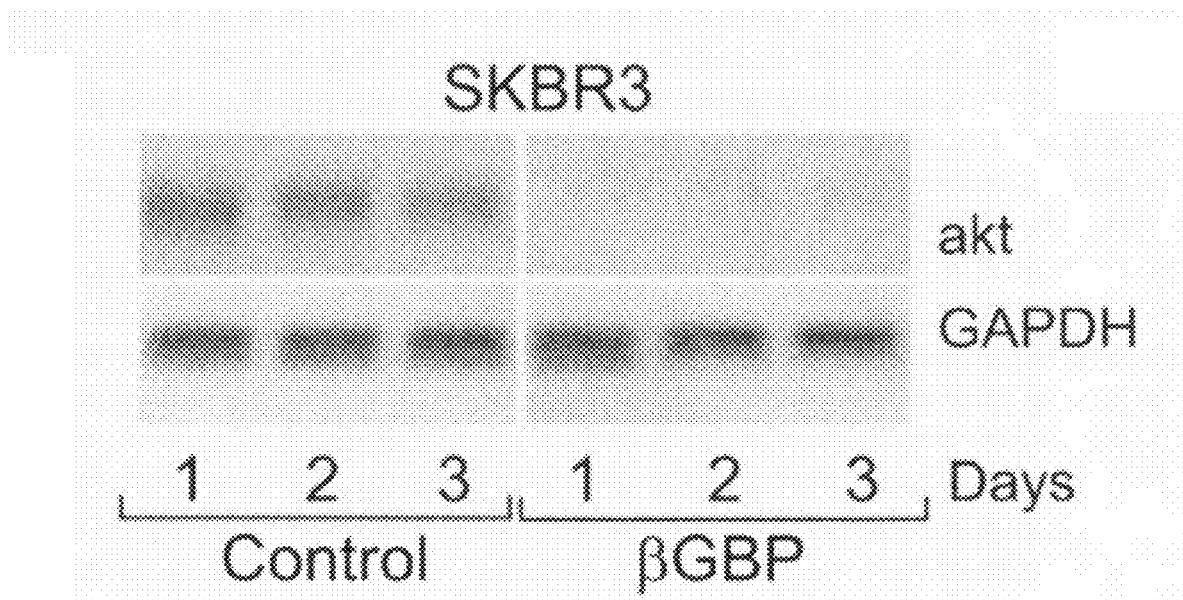
Figure 1J:
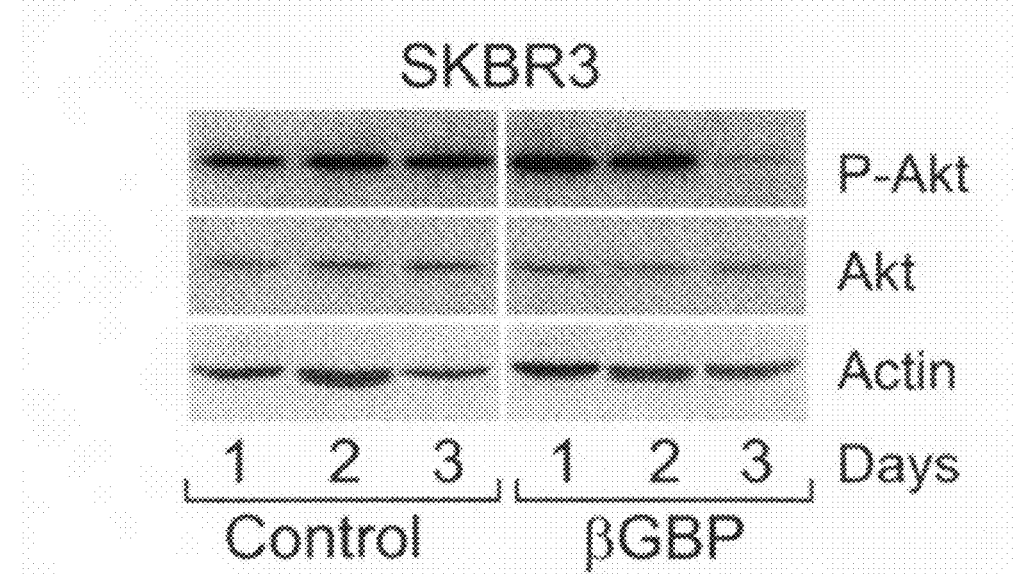
Figure 2A:
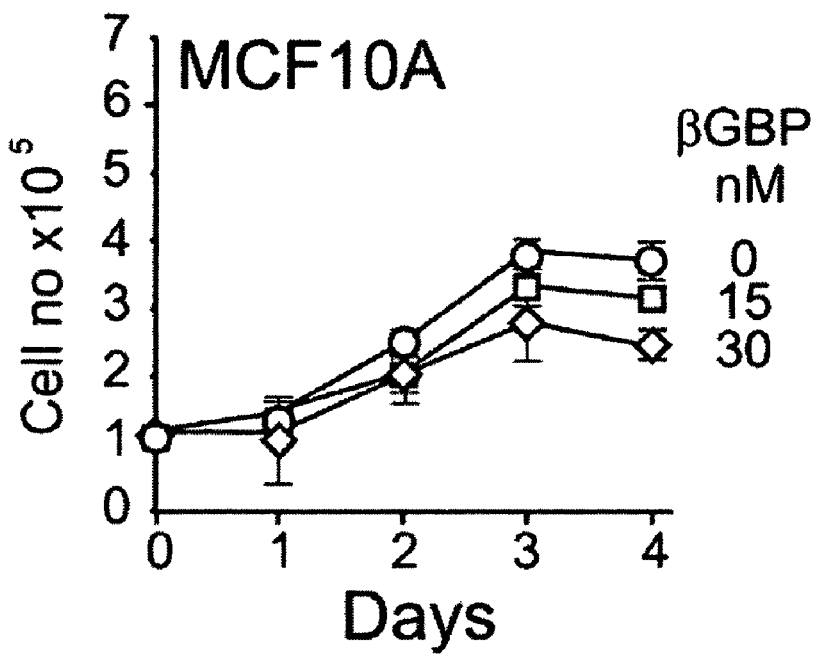
(FIG. 2A-C) Rate of cell proliferation and cell response to Hu-r-βGBP. Values are means from triplicate cultures +/−SEM.
Figure 2B:
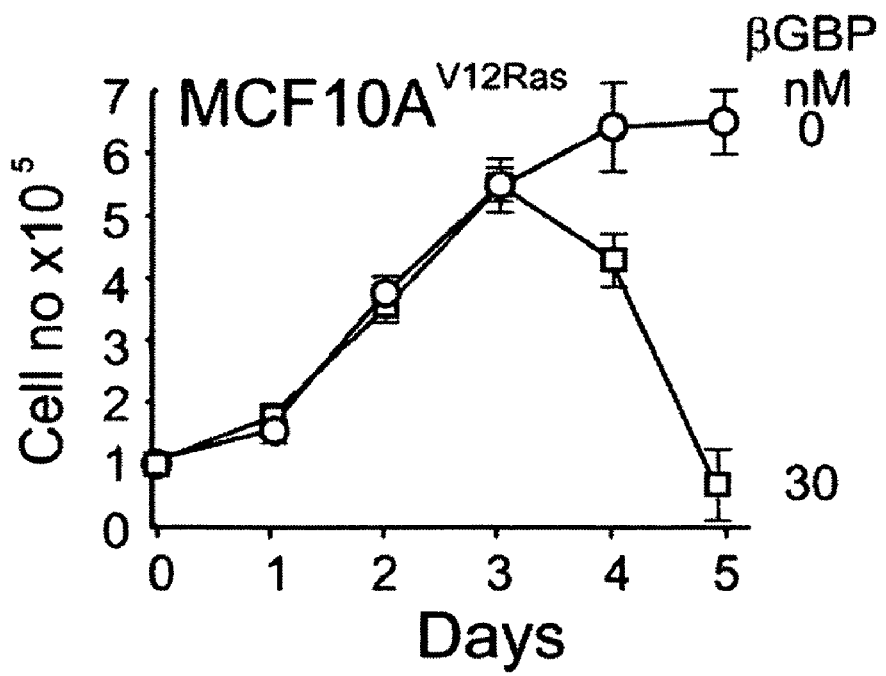
Figure 2C:
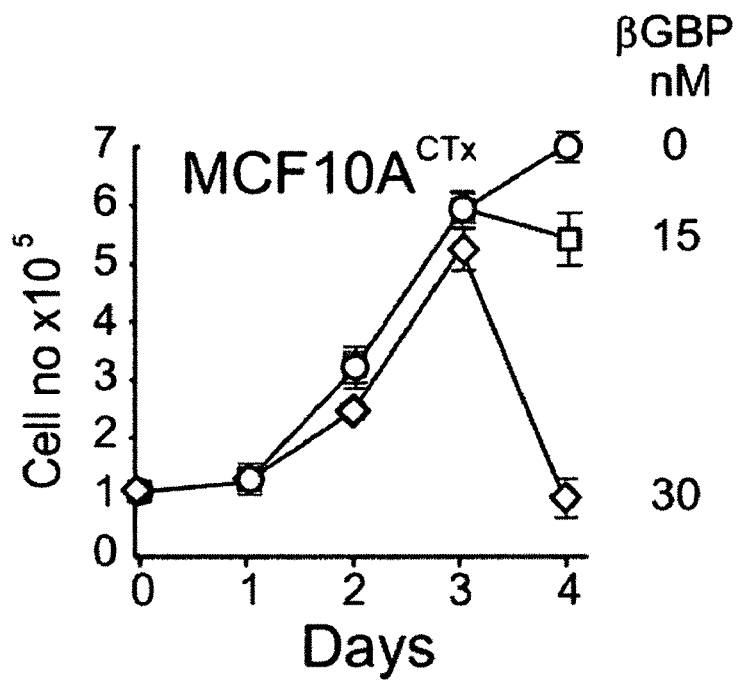
Figure 2D:
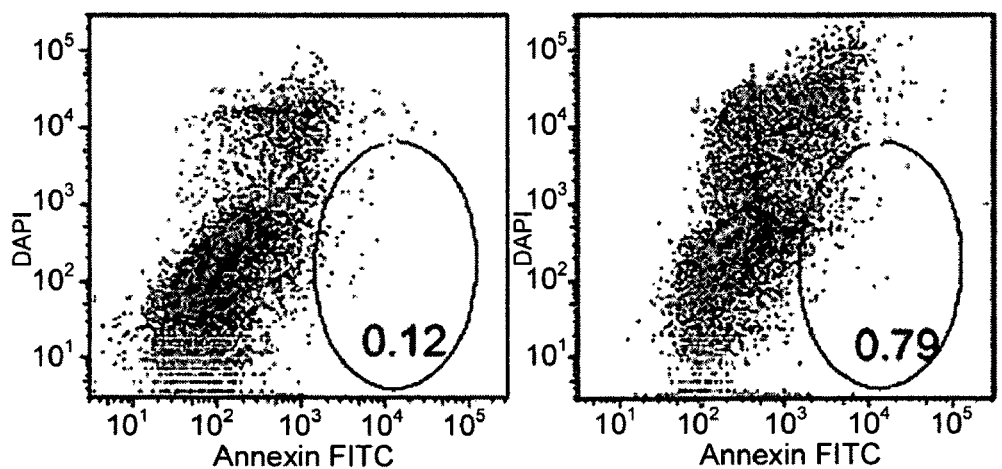
(FIG. 2D-F) Apoptosis assessed by Annexin V staining at day three after seeding. Apoptotic cells in circled areas. Values are percentages of cells in apoptosis. Left panels: controls; right panels: cells treated with 30 nM Hu-r-βGBP.
Figure 2E:
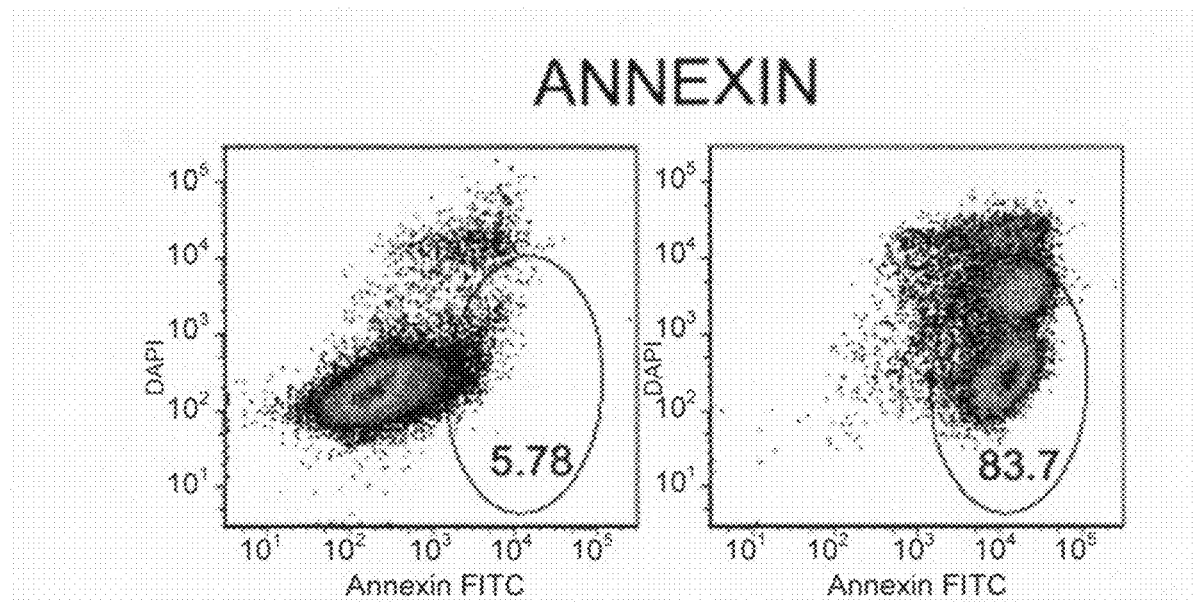
Figure 2F:
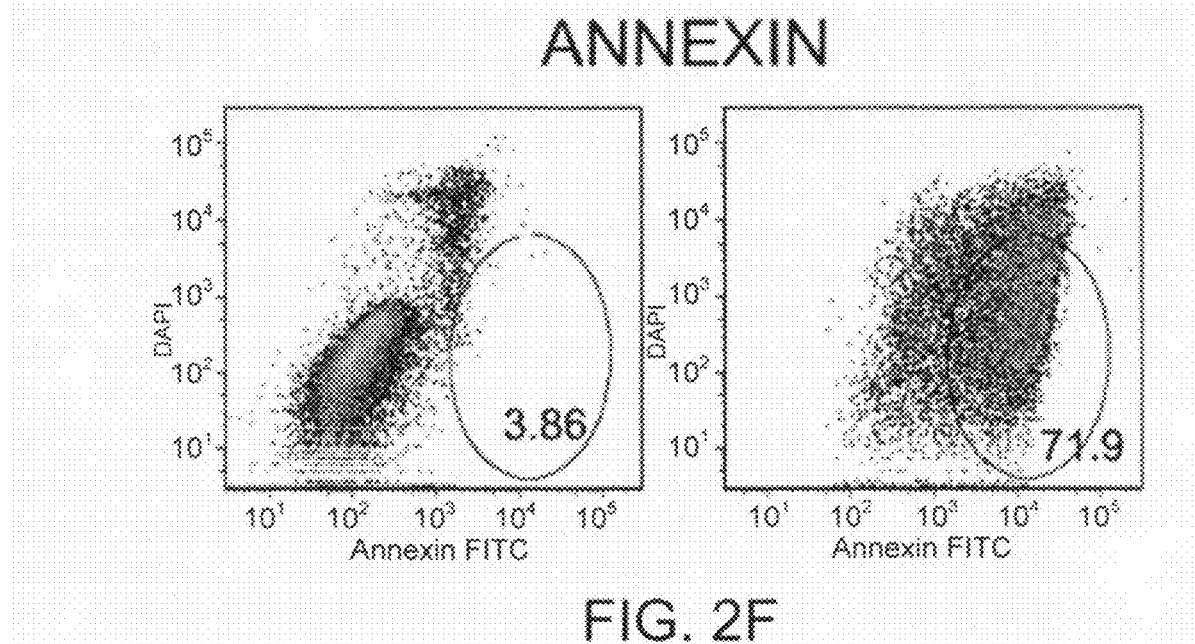
Figure 2G:
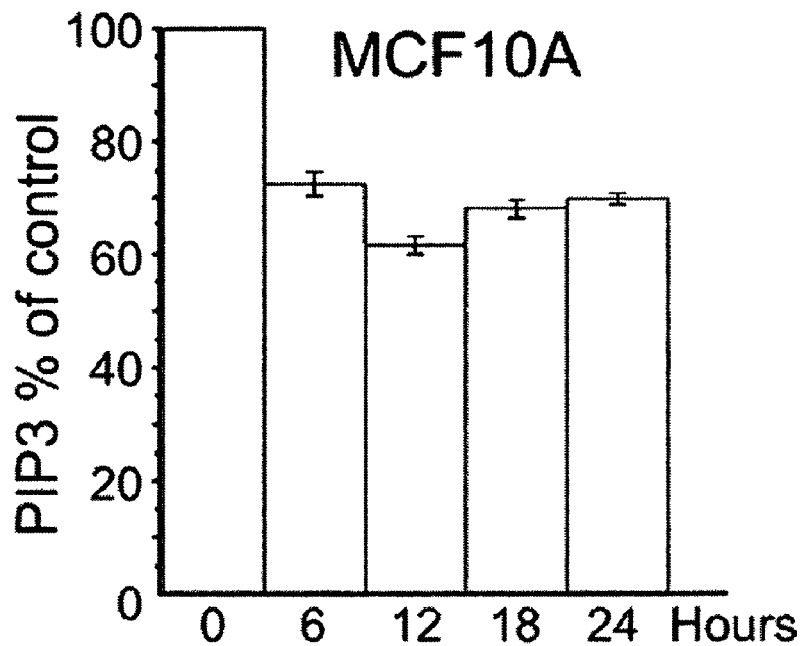
(FIG. 2G-I) Inhibition of Class IA PI3K by 30 nM Hu-r-βGBP assessed as described in FIG. 1. Values are means from triplicate readings +/−SEM.
Figure 2H:
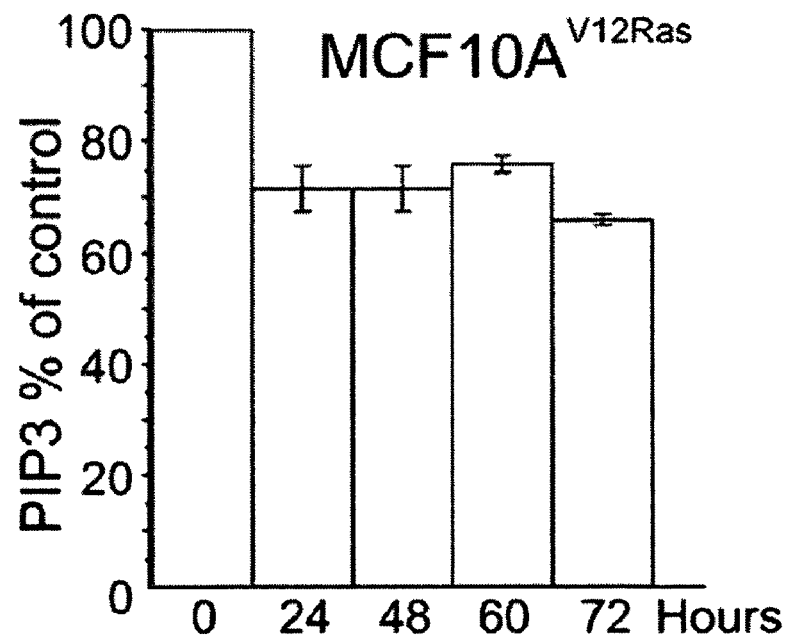
Figure 2I:
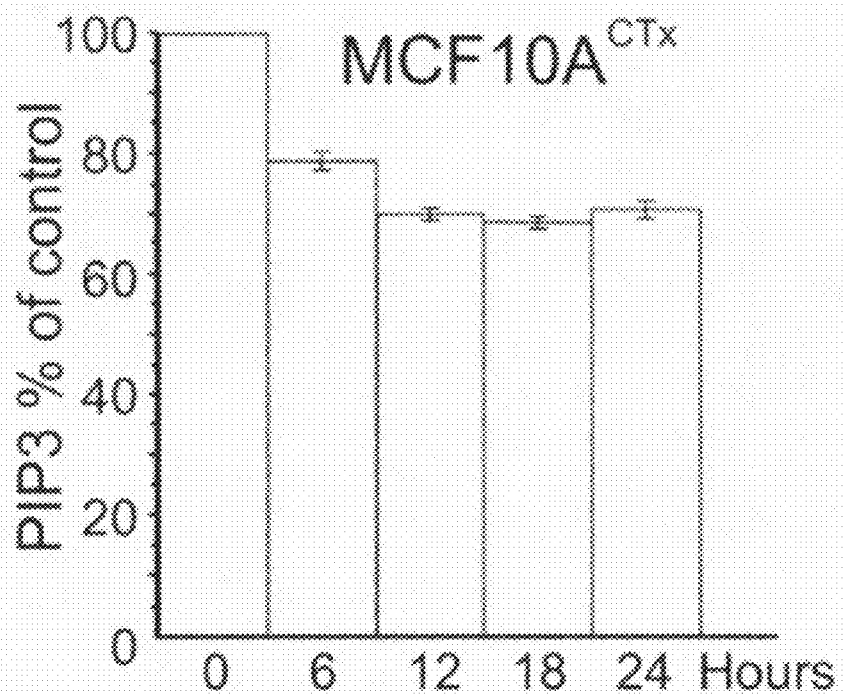
Figure 2J:
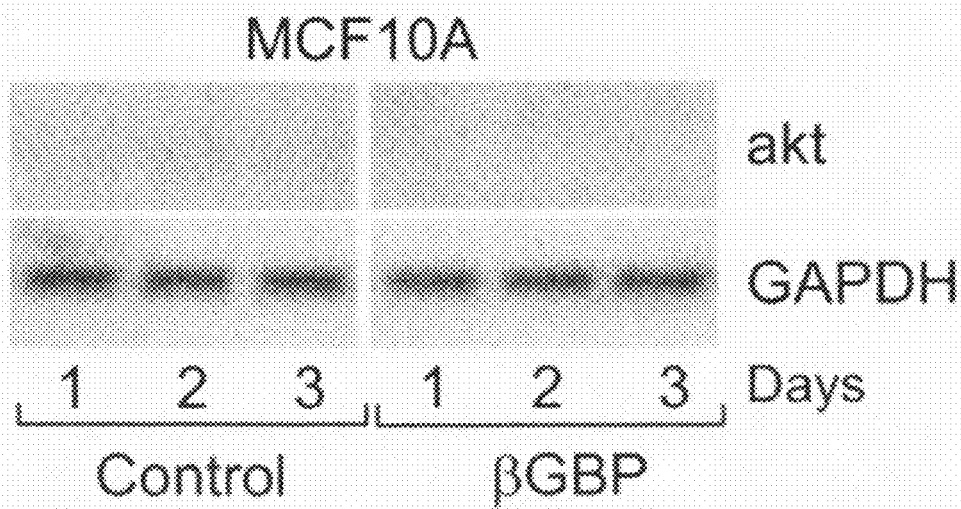
(FIG. 2J-L) akt mRNA and GAPDH mRNA levels. Left panels: controls; right panels: cells treated with 30 nM Hu-r-βGBP.
Figure 2K:
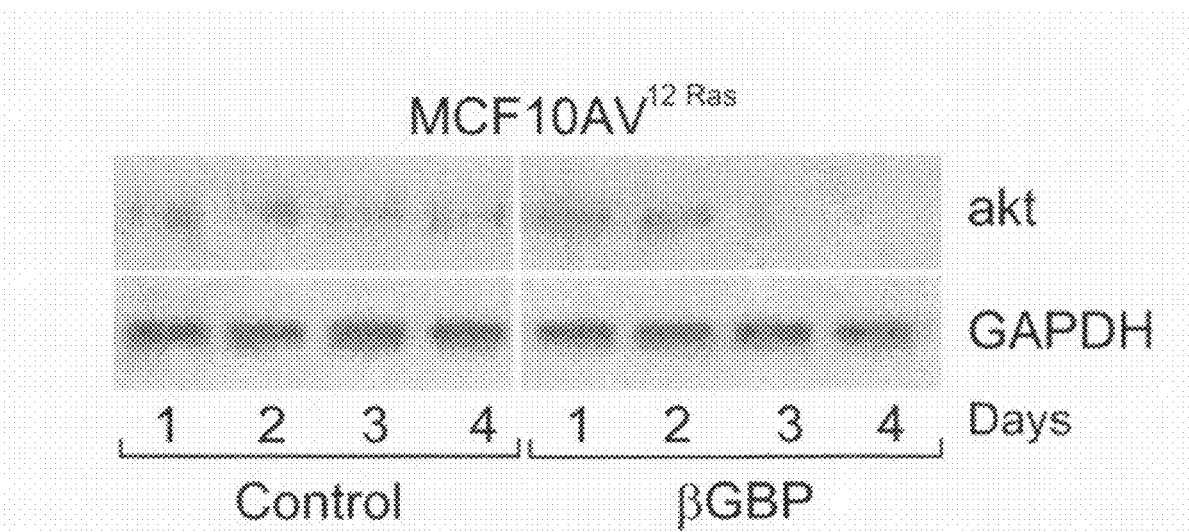
Figure 2L:
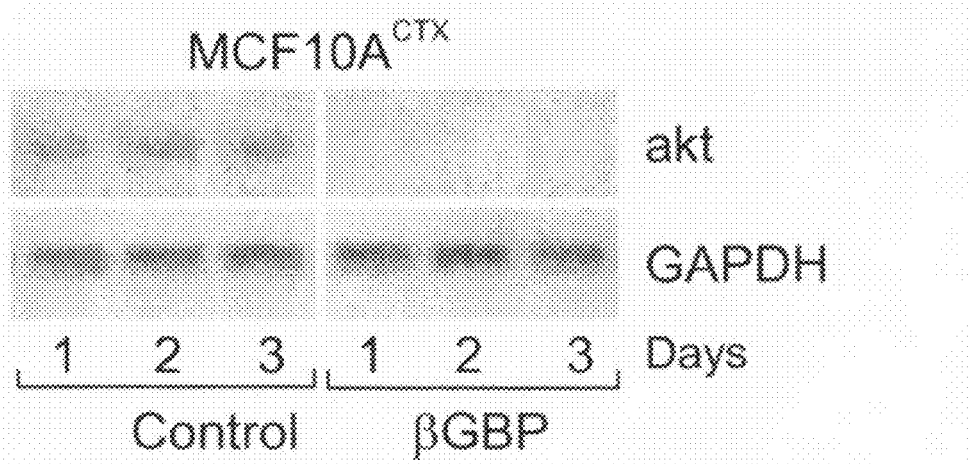
Figure 2M:
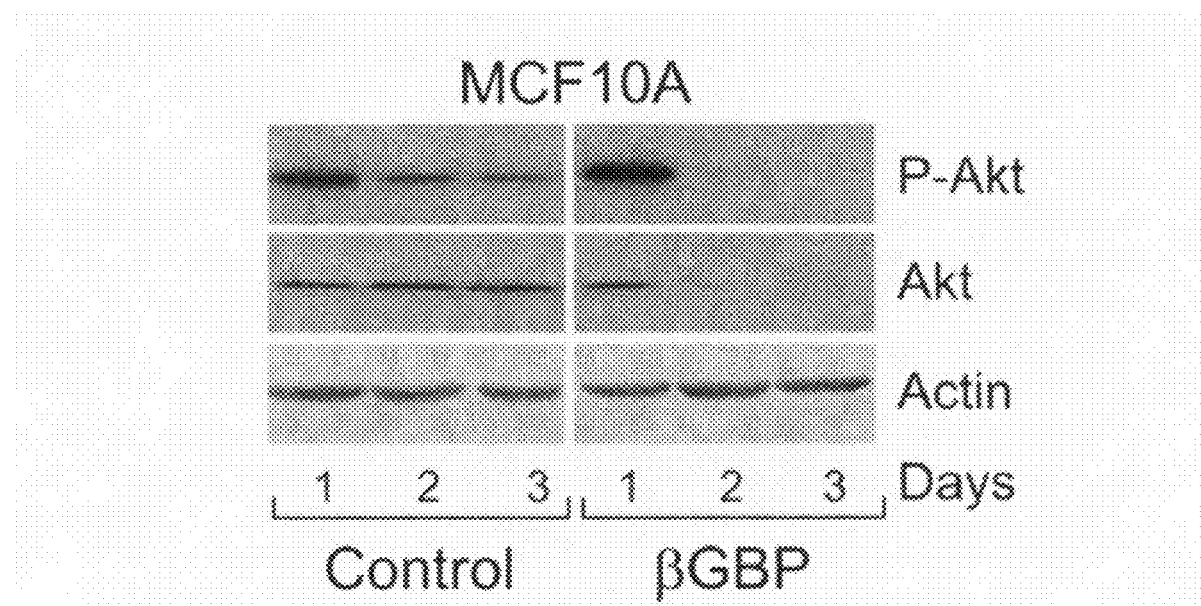
(FIG. 2M-O) Phosphorylated (Ser 473) Akt and total Akt protein. Left panels: controls; right panels: cells treated with 30 nM Hu-r-βGBP.
Figure 2N:
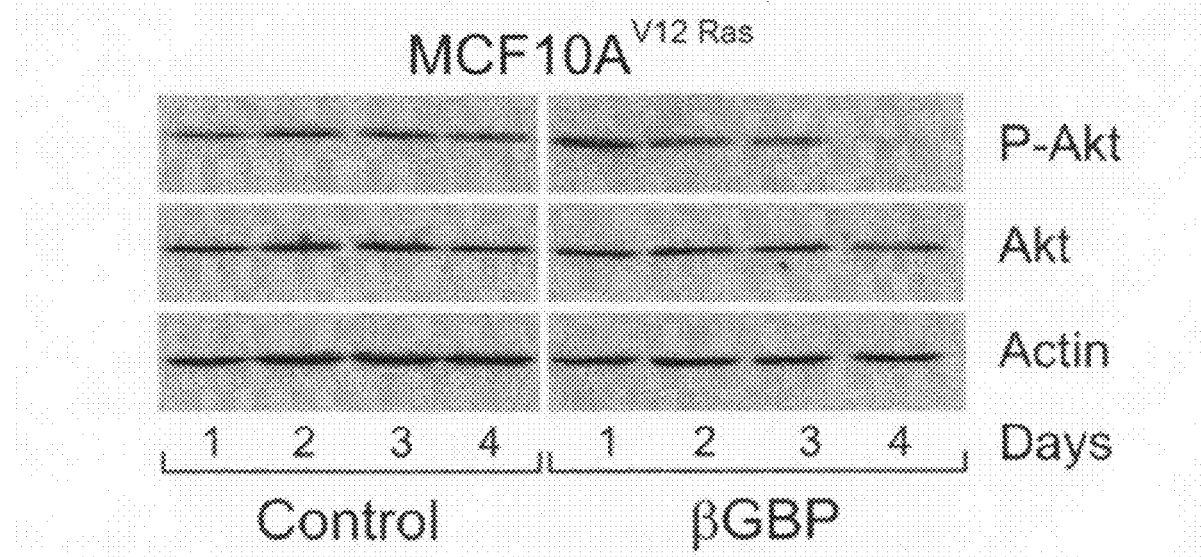
Figure 2O:
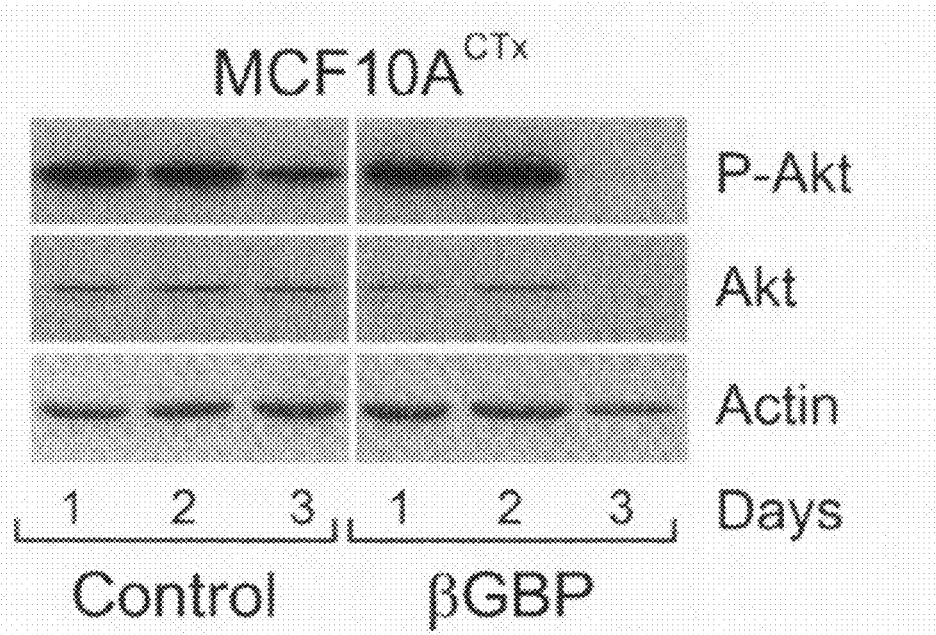

FIGS. 1E and H demonstrates that downregulation of PI3K activity was an early event already present at hour six after the addition of βGBP and maintained throughout the period of observation. Framed within a time sequence, these results show that addition of βGBP to the BT474 and SKBR3 cells resulted in downregulation of PI3K activity, loss of akt gene expression, loss of Akt function and apoptosis.

ERK, akt Gene, PI3K and βGBP are Functionally Linked

While showing that cancer cells driven by strong mitogenic pressure are unresponsive to the growth inhibitory effect of the βGBP cytokine (Mallucci et al., 2003, Wells and Mallucci 1991), the evidence of FIG. 1 suggests that to elevated mitogenic input, corresponding elevated survival signalling may create conditions that would protect mitogenic expansion, but which βGBP can interrupt by downregulation of PI3K activity and consequent block of akt gene function.

In order to test the validity of this assumption the inventors experimentally enforced mitogenic pressure in non cancerous cells. The cells used were: spontaneously immortalized MCF10A mammary ductal cells which exhibit normal-like behaviour (Soule et al., 1990), MCF10A cells stably transfected with constitutively active p21 Ras mutated at valine 12 (Schulze et al., 2001) (MCF10A$^{V12Ras}$), which strongly activates Raf-ERK signalling (Repasky et al., 2004), and MCF 10A cells where mitogenic input was enhanced by the addition of cholera toxin (MCF10A$^{CTx}$) which increases ERK activity via adenyl cyclase upregulation (Alberts et al., 2002).

The following concepts were examined: whether mitogenic pressure would affect proliferation rate and cell response to βGBP; whether there would be correlation between mitogenic input and akt mRNA levels; whether βGBP would affect PI3K activity and whether there would be correlation between PI3K activity and akt gene expression.

It was found that cell proliferation was boosted both by V12Ras and by cholera toxin and that the response to βGBP, abrupt cell death after 2-3 cell replication cycles, mimicked that of the BT474 and SKBR3 cells, in contrast with the minor effect exerted by βGBP in the naïve MCF10A cells (FIGS. 2 A-C and D-F). A correlation was also found between mitogenic pressure and akt gene expression, as shown by changes in akt mRNA levels which, barely detectable in the naïve cells, became more markedly expressed where the mitogenic input had been raised, whether by V12 Ras or by cholera toxin (FIG. 2 J-L, left panels).

Examination of whether βGBP would affect PI3K activity and akt gene expression showed that in all cases βGBP brought down and maintained PI3K activity below basal levels (FIG. 2 G-I) regardless of mitogenic input, with a pattern similar to that observed in the ErbB2 positive cells, but with a delay from 6 to 24 hours, in accord with the later disappearance of akt mRNA (FIG. 2 K, right panel), where the cells were driven by the strong mitogenic signalling imposed by V12 Ras. Similarly to the cells of FIG. 1, in all the above cells, downregulation of PI3K activity resulted in virtual absence of akt mRNA (FIG. 2 J-L, right panels) and consequent loss of Akt function (FIG. 2 M-O). Notably, the time sequence of PI3K inhibition, loss of akt mRNA and loss of Akt, copied the pattern observed in the BT474 and SKBR3 cells.

It is of particular significance within a therapeutic context that in the naïve normal-like MCF10A cells, which have low levels of akt mRNA, inhibition of PI3K activity and loss of akt gene function did not lead to apoptosis, as it indicates that loss of survival signalling is not harmful in the absence of abnormal mitogenic pressure. Without wishing to be bound by theory, this is one conceivable explanation for the selective effect of βGBP which, while killing cancer cells, including their drug resistant derivatives (Mallucci et al., 2003, Ravatn et al., 2005), causes no harm to normal cells (Wells and Mallucci 1991).

The above data, together with those of FIG. 1, indicate that strong mitogenic pressure as represented by the degree of ERK phosphorylation, whether constitutive or induced (FIG. 3), is coupled to elevated akt gene expression. Collectively, the observations described herein endorse a model where enhanced ERK activity enhances cell survival by upregulating akt gene expression, for which PI3K activity is a requirement (FIG. 4A), and where, by down-regulating PI3K activity and negating akt gene function, βGBP interrupts cancer cell reliance on survival signalling and leads cells to apoptotic death (FIG. 4B).

It is noteworthy within the ERK/akt gene context that the observations presented herein bring to attention a new functional aspect in transcriptional control which extends the role of ERK from the activation of cell cycle promoting genes (Karin and Hunter 1995) to the activation of the akt gene, which promotes survival. Notably, no evidence was found that raising active ERK levels, whether by V12Ras or by cholera toxin, had any effect on PI3K activity.

Cancer Phenotype and Cell Vulnerability

The evidence that in the MCF10A cells a shift in phenotypic behaviour as a consequence of enforced mitogenic pressure changed the cells' response to βGBP to mimic that of the SKBR3 and BT474 cancer cells, raises the question of whether in cancer cells a shift towards a more aggressive condition would increase their vulnerability to βGBP.

MCF-7 breast cancer cells were therefore examined. These cells have low levels of ErbB2 and do not exhibit aggressive behaviour (Karanugaran et al., 1996). MCF-7 cells were examined in their naïve state and when also treated with cholera toxin (MCF-7$^{CTx}$).

Figure 5A:
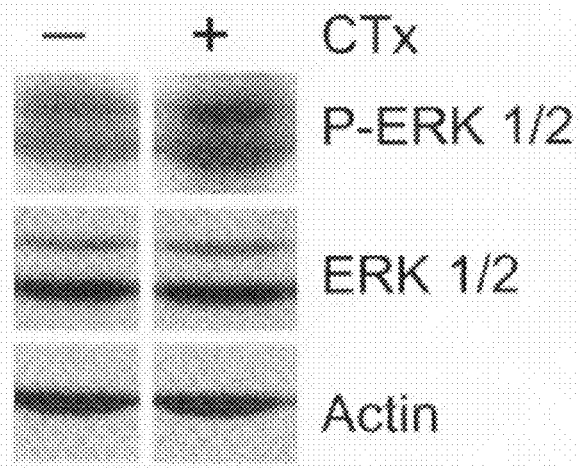
(FIG. 5A-C) Effect of cholera toxin (100 ng/ml) on ERK phosphorylation, cell proliferation and akt gene expression. Values in B are means of triplicate cultures +/−SEM.
Figure 5B:
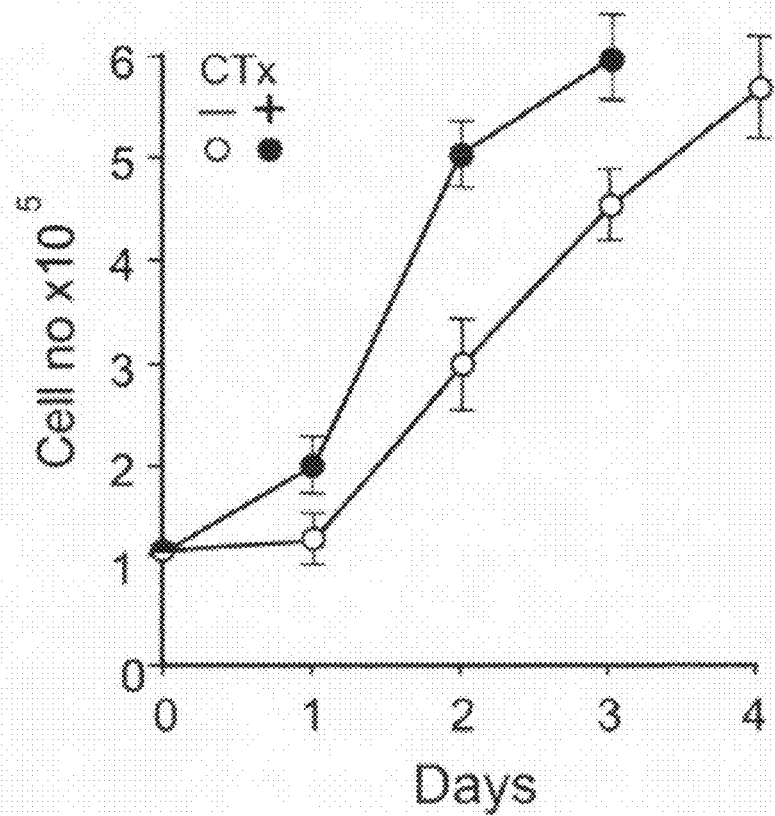
Figure 5C:
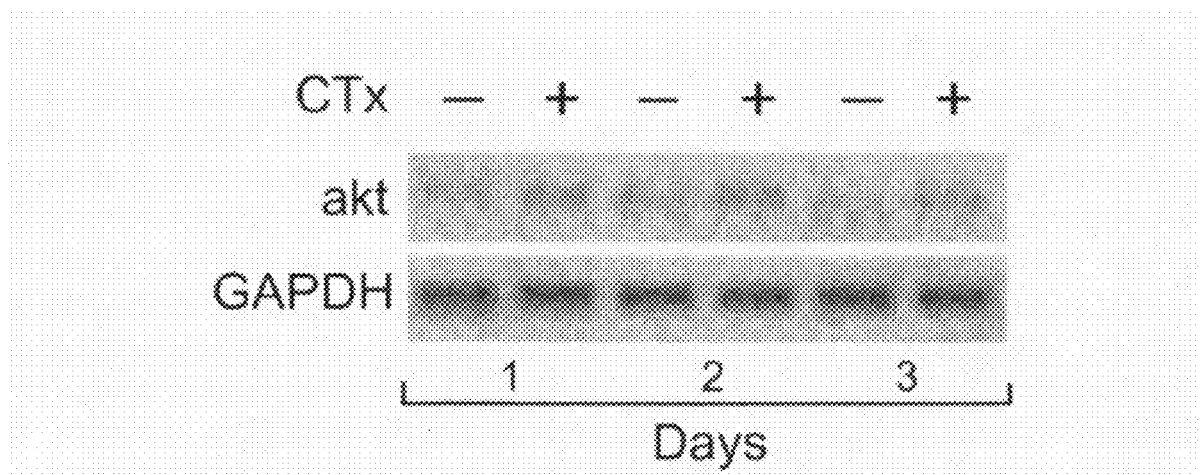
Figure 5D:
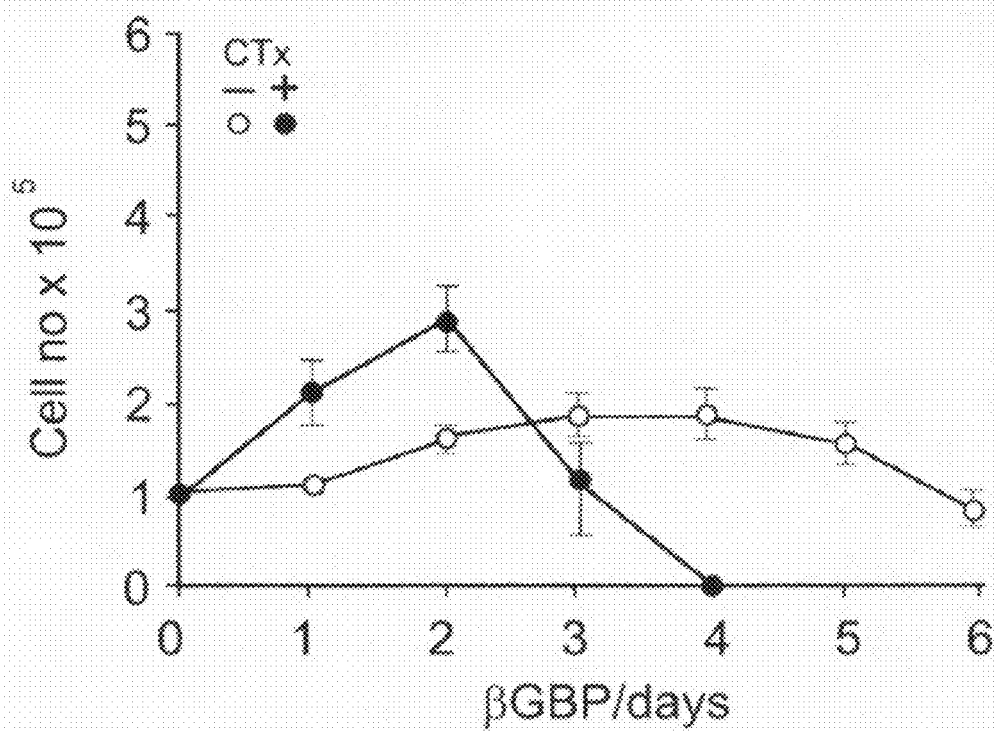
(FIG. 5D) Growth curves in response to treatment with 20 nM Hu-r-βGBP added at hour 3 from seeding in naïve cells and in cells treated with 100 ng/ml cholera toxin. Values are means from triplicate cultures +/−SEM.

It was found that cholera toxin raised active ERK levels, accelerated cell proliferation and accentuated akt gene expression, thus changing the phenotypic behaviour of the cells (FIG. 5A-C). Examination of their response to βGBP showed that, while overriding the growth inhibitory effect that βGBP exerted on the naïve MCF-7 cells, as reported previously (Ravatn et al., 2005), the MCF-7$^{CTx}$ cells succumbed to total death ahead of the naive counterparts (FIG. 5D), thus confirming the proof of the principle that where ERK activity and akt gene expression are enhanced, abolition of akt gene function can result in greater cell vulnerability.

Next it was investigated whether in the MCF-7$^{CTx}$ cells PI3K was again a primary responder to the action of βGBP and, if so, whether negation of akt gene expression would be a consequence of the inhibition of PI3K activity.

Therefore time scale experiments were carried out using βGBP in parallel with wortmannin (Powis et al., 1994) and LY29400 (Vlahos et al., 1994). Both compounds are pharmacological inhibitors of the p110 catalytic subunit of PI3K (Walker et al., 2000, Wymann et al., 1996), and were added at concentrations which would produce an effect similar to that of βGBP.

Figure 5E:
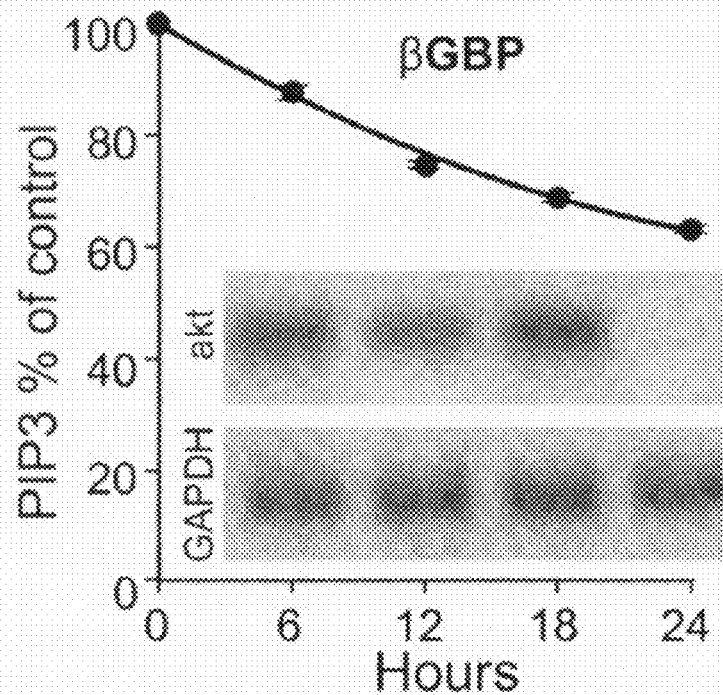
(FIG. 5E-G) Relationship between downregulation of PI3K activity and akt mRNA levels in MCF-7$^{CTx}$ cells treated with 20 nM Hu-r-βGBP, 10 nM wortmannin or 20 nM LY294002 added at hour 3 from seeding. PIP3 values are means of triplicate readings +/−SEM.
Figure 5F:
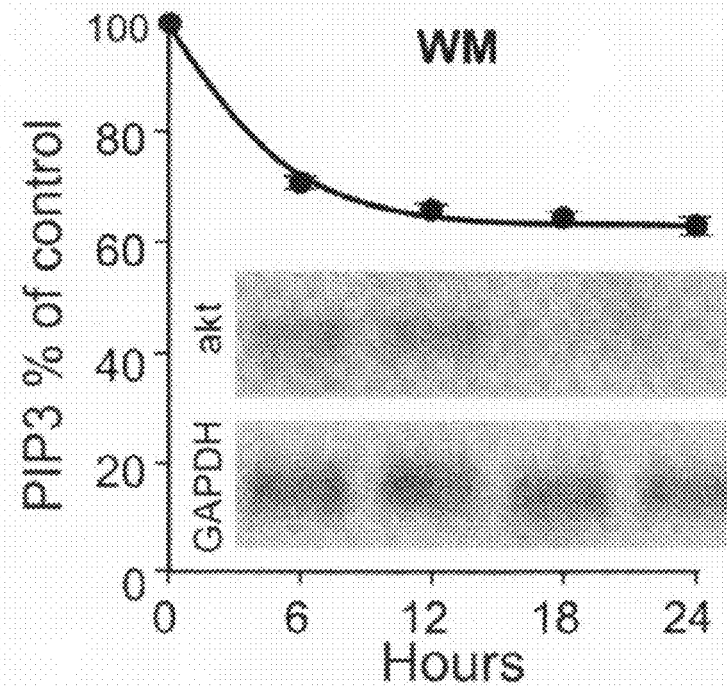
Figure 5G:
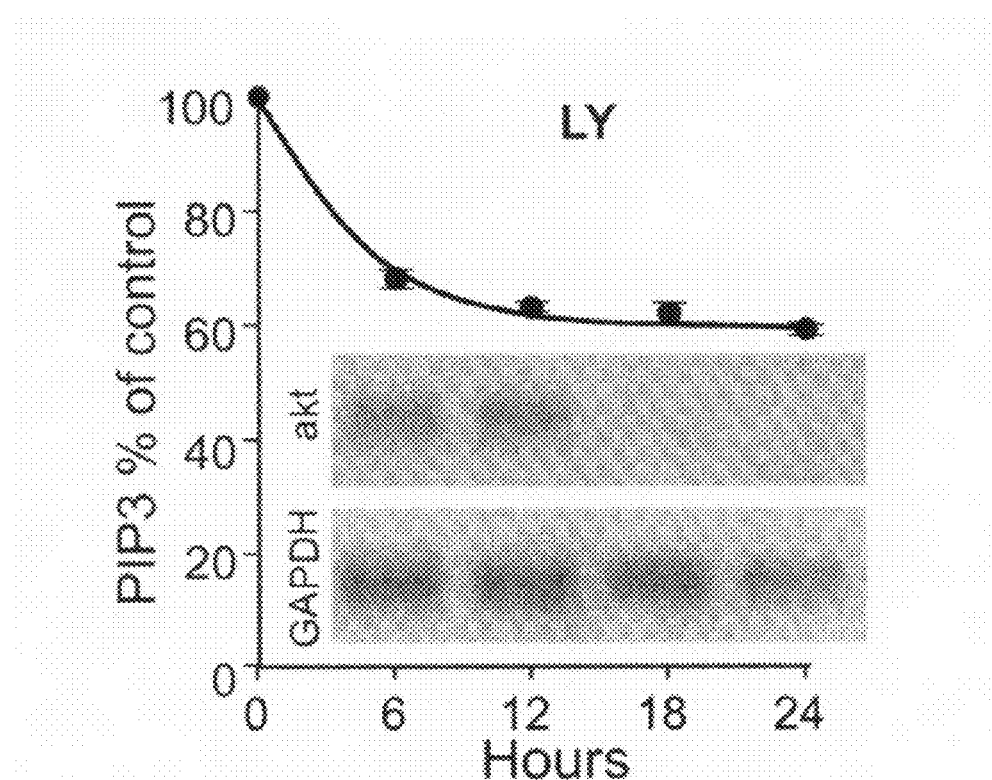

PI3K activity and akt mRNA levels were assessed at different time points. Evidence was found to indicate that PI3K activity is a necessary requirement for akt gene expression and that basal or close to basal endogenous levels are sufficient. FIG. 5E-G shows that βGBP lowered PI3K activity to a similar extent as the two inhibitors, but with a more gradual kinetic, in line with the action of a physiological effector molecule, and that akt gene expression was negated when PI3K activity had similarly descended by an approximate 35% quantum below basal levels, in all three instances.

The PI3K/Akt signalling cascade is under intensive investigation for its role in oncogenic transformation and for its critical contribution to aggressiveness and resistance to therapies (Lu et al., 2003, Chen et al., 2005, Morgensztern and McCleod 2005). The present inventors have identified the βGBP cytokine as a selective PI3K targeting agent, provides the first evidence for functional dependence between PI3K and the akt gene and the first evidence for an effective treatment of aggressive cancer cells via therapeutic silencing of the akt gene by a physiological molecule.

In conclusion, the present inventors have shown that, contrary to its ability to arrest cell cycle progression both in normal (Wells and Mallucci 1991) and in some cancer cells (Mallucci et al., 2003), βGBP was unable to affect cell proliferation in cells driven by strong mitogenic input. However, by controlling a functional link between PI3K and the akt gene, βGBP does have strong therapeutic efficacy without compromising cells which exhibit normal-like behaviour.

The inventors hypothesise that ERK, the akt gene, PI3K and βGBP are mechanistically linked and that PI3K is the pivotal element on which βGBP acts. Functional inhibition of the p110 catalytic subunit of class IA PI3K by βGBP is followed by abrogation of akt gene expression and by apoptotic death in cells where ERK and akt mRNA levels are high, but not otherwise. The similarity of the effect of βGBP with that of wortmannin and LY294002, in regard of both inhibitory pattern and time required for the inhibitory action to come into effect (FIG. 5 D-F), suggests that, similarly to the two inhibitors, βGBP may induce conformational changes which would reduce the functional ability of the regulatory pocket site of the p110 catalytic subunit of PI3K (Walker et al., 2000).

PI3 Kinase and Ras are functionally linked. This link is suppressed by βGBP. The p110 catalytic subunit of PI3 Kinase is inhibited by βGBP. Thus in normal cells Ras-MAPK signalling is blocked by βGBP. PI3 Kinase activity is downregulated by βGBP, leading to suppression of Ras-GTP loading, consequent loss of MAPK activation and, in the context of cells which retain a sensitivity to the growth inhibitory properties of βGBP, cell proliferation is blocked. In cells which no longer respond to βGBP with inhibition of growth (for example, cells as targeted by the present invention, such as persistently dividing cells), the eventual result of the inhibition of PI3K activity is different. Instead, in persistently dividing cells of the present invention, no effect on Ras-MAPK loading is seen as the mitogentic input is too great. However, in such cells, the silencing of akt gene expression ultimately results in apoptosis.

The dependence of gene expression on PI3K activity that is shown herein is a new aspect in gene control which may not be limited to the akt gene.

It is of interest within the context of PI3K inhibition and suppression of akt gene function, that the mapping of the gene encoding βGBP (Chiariotti et al., 1991) in the sis/PDGFB homology region (mu-chromosome 15E/Hu-chromosome 22 q12-q13) (Baldini et al., 1993), a syntenic group which undergoes deletion and translocation in a number of human tumors (Aurias et al., 1984, Turc-Carel et al., 1998, Bridge et al., 1990, Rey et al., 1993) brings to attention the βGBP gene as a prospective tumor suppressor gene.

In Vivo Efficacy and Safety

βGBP can totally prevent the appearance of tumours in SCID mice. $5 \times 10^6$ ST4 (Human malignant T cell leukaemia) cells were injected subcutaneously at day 0. Hu-r-βGBP was administered from day 1 to day 16 by subcutaneous injection. The results are indicated in table 1 below.

TABLE 1

| βGBP ng/mouse | Tumour size (mm) at day 42 | Tumour size (mm) at day 90 |
|---|---|---|
| 0 | 8, 10, 16, 16 | + + + + |
| 20 | 0, 0, 0, 8 | 0, 0, 0, + |
| 200 | 0, 0, 8, 8 | 0, 0, +, + |
| 400 | 0, 0, 0, 0 | 0, 0, 0, 0 |

Key:
0 = No tumour
+ = mouse mortality

Efficacy of βGBP Against Colon Cancer at Low Doses

As described above βGBP is known to inhibit growth and/or promote apoptosis in cells from a range of cancer types. However, in experiments to screen the effects of βGBP in a range of cancer types it was surprisingly noted that βGBP was effective in colon cancer cells at a much lower dose than is observed for other cancer types.

In breast cancer, ovarian cancer, oral cancer, prostate cancer and leukaemia cells tested for pro-apoptotic responses to βGBP, the effective dose in cell culture was 15-30 nM. In colon cancer cells the effects of βGBP were observed at much lower concentrations.

Figure 6A:
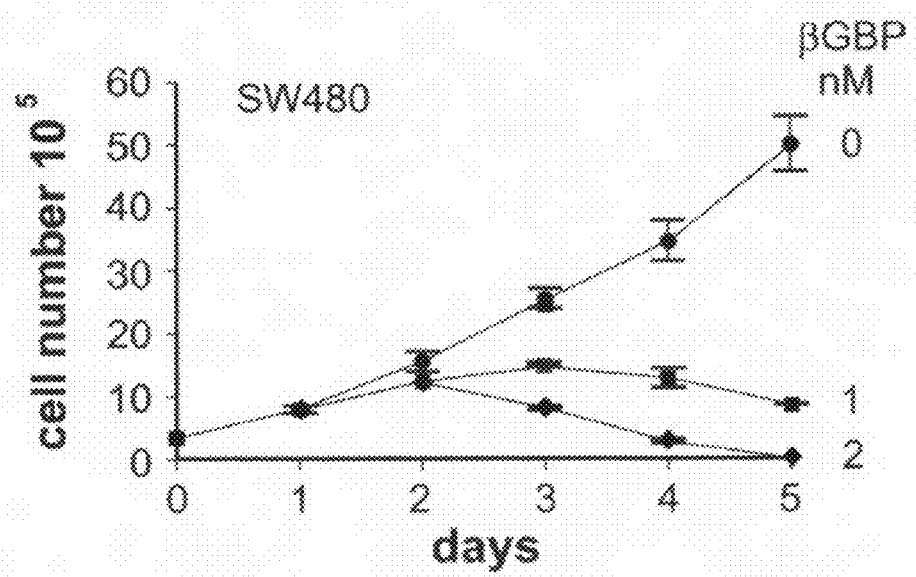
FIG. 6A) SW480, (FIG. 6B) SW620 and (FIG. 6C) LoVo.
Figure 6B:
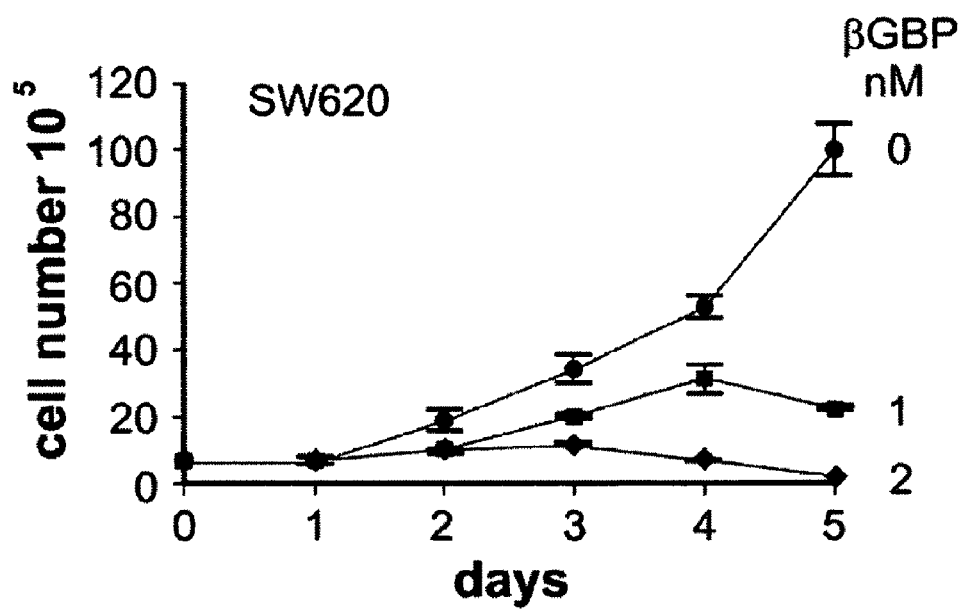
FIG. 6 shows the rate of cell proliferation and cell response to Hu-r-☐GBP for three colon cancer cell lines. Hu-r-βGBP was added at hour 3 after seeding.
Figure 6C:
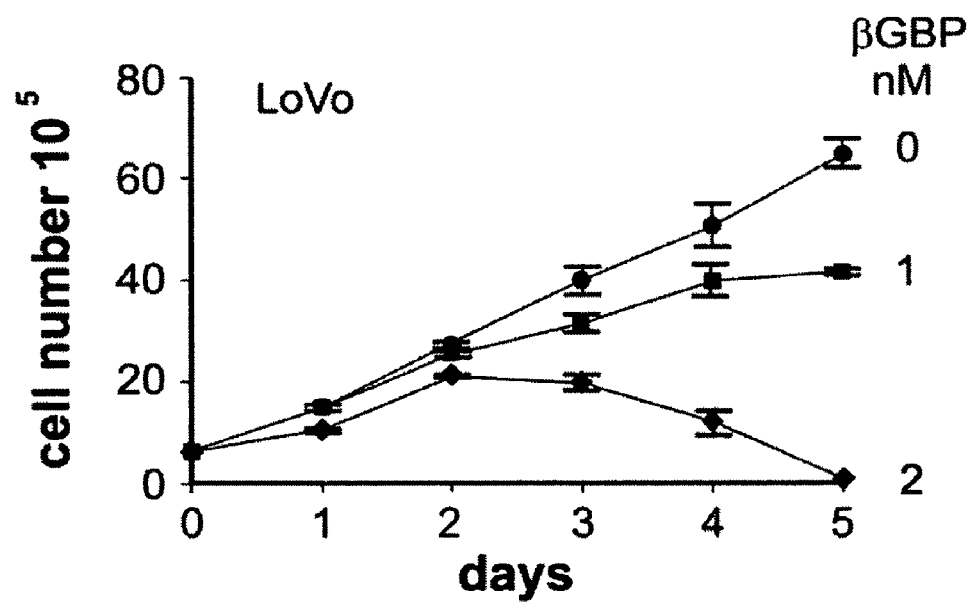

To confirm these observations three colon cancer cell lines were investigated, SW480, SW620 and LoVo. Cells were grown in culture and incubated with βGBP at varying concentrations. It was found that all of the colon cancer cell lines were much more susceptible to the pro-apoptotic effects of βGBP than other cancer cell lines. Concentrations as low as 1-2 nM have been observed as effective in inducing apoptosis (FIG. 6). It is possible that in some circumstances even lower concentrations of βGBP may be effective.

Similar kinetics for initial growth, followed by a sharp decline in cell numbers were observed (FIG. 6) for each colon cancer cell line, in a manner similar to that previously observed for BT474 cells and SKBR3 cells (FIGS. 1 A and C), MCF10A$^{V12Ras}$ cells and MCF10A$^{CTx}$ cells (FIGS. 2 B and C), and MCF-7 cells treated with cholera toxin (FIG. 5). This demonstrates that βGBP has an equivalent effect on colon cancer cells as it does on other cancer cell lines, but at concentrations 15 to 30 times lower.

This result is unexpected given the broadly similar effective concentration range for the inhibition of growth effect or the induction of apoptosis in other cancer cell lines by βGBP. Thus βGBP appears to be particularly suitable for the treatment of colon cancer since therapeutic effects may be possible at much lower βGBP doses.

SUMMARY

The present invention therefore relates to several therapeutically relevant aspects. Firstly, inhibitory effects on the activity of the enzyme PI3 Kinase have been demonstrated for βGBP.

Firstly, the evidence that mitogenic pressure, whether endogenous or enforced, makes cancer cells highly vulnerable to treatment with the βGBP cytokine (FIGS. 1 and 5), suggests that this physiological molecule may have particular therapeutic relevance to the treatment of aggressive cancers.

Secondly, the evidence of FIG. 2 where naïve MCF10A cells, which have relatively low levels of active ERK and low levels of akt mRNA, are not harmed by βGBP challenge, suggests that βGBP has ability to selectively induce apoptosis according to the particular molecular context of the cell, a property not shared by pharmacological compounds. Significantly, the evidence of FIG. 3 also suggests that where an increase in mitogenic signalling is the prime occurrence amongst events that lead to oncogenesis, nascent cancer cells could be eliminated in the healthy organism by the endogenously produced βGBP in a surveillance role (Mallucci et al., 2003).

Thirdly, while the extent of mutation multiplicity, high in breast cancer (Sjoblom et al., 2006), may require multiple drug combinations with implicit synergistic toxicity, our findings indicate that the disabling by βGBP, a physiological effector molecule, of one single gene, akt, can bypass mutational complexity and chemotherapeutic disadvantages. Thus reducing the expression of the akt gene, possibly using alternative agents other than βGBP, is a new therapeutic route for the treatment of cancer, in particular, breast cancer.

Fourthly, colon cancer cells are particularly susceptible to apoptosis induced by βGBP. Thus colon cancer is a particularly suitable target for treatment with pGBP.

Finally, while providing a model for the clinical use of βGBP in aggressive cancers, the present invention also provides a mechanistic rationale for the use of βGBP in other conditions in which undesirable cell division occurs, in particular, those where said cell division is characterised by aggressive or hyperproliferative behaviour such as self immune responses (e.g. autoimmune conditions) and immune responses against transplanted organs, tissues or cells.

EXAMPLES

Example 1

Effect of βGBP on Cells Overexpressing ErbB2

Cell culture: BT474 cells were cultured in DMEM/F12 medium with 10% fetal calf serum (FCS) (Invitrogen, UK) and 20 µg/ml insulin (Sigma, UK); the SKBR3 cells were grown in DMEM medium (Invitrogen UK) plus 10% FCS. Cultures were incubated at 37° C. in a humidified atmosphere of 5% CO2 in air.

$1 \times 10^5$ cells were seeded per 25 cm$^2$ flask, or $3 \times 10^5$ per 75 cm$^2$ flask. Sufficient numbers of flasks were seeded in parallel to allow for individual flasks to be consumed in the process of monitoring cell numbers (i.e. growth rates), apoptosis, PI3K activity, akt mRNA levels, Akt protein levels and phosphorylated Akt (P-Akt) protein levels as discussed below. Unless otherwise indicated results correspond to one flask of cells.

Growth rates: Cells were removed from the flasks by trypsinisation and counted in a haemocytometer to assess cell numbers at time points of 1, 2, 3, 4, and 5 days for BT474 cells, SKBR3 cells, MCF10A$^{V12Ras}$ cells and MCF10A$^{CTx}$ cells. MCF10A cells were monitored at 1, 2, 3, and 4 days. Cell numbers were determined in triplicate.

βGBP: Human recombinant βGBP (Hu-r-βGBP) was expressed in *E. coli* BL21(DE3) using hGal-1 cDNA in PET21a (Hirabayashi et al., 1989), purified by lactose-agarose (Sigma, UK) affinity chromatography and purity assessed by MALDI-TOF.

Hu-r-βGBP was added to cell cultures at a concentration of 15 nM or 30 nM at hour 3 after seeding cells. Control cells (0 nM βGBP) were also prepared. Hu-r-βGBP was maintained at the appropriate concentration (0 nM, 15 nM or 30 nM respectively) throughout the time course of the cell culture.

Cytofluorimetry: Apoptosis was monitored using four criteria as outlined below. Control cells (0 nM Hu-r-βGBP) were compared to cells cultured with 30 nM Hu-r-βGBP at a time point of 3 days for BT474 cells and 4 days for SKBR3 cells. Cells were washed and released from the flasks using trypsin and resuspended in Phosphate buffered Saline (PBS).

Tetramethylrhodamine ethyl ester (TMRE) (Molecular Probes/Invitrogen, UK) staining was used to assess loss of mitochondrial membrane potential. Cells suspended in PBS were incubated at 37° C. for 20 minutes in 40 uM TMRE, centrifuged, washed in PBS and resuspended in 500 ul of 200 ng/ml 4', 6-Diamidino-2-phenylindole dihydrochloride (DAPI) (Sigma, UK) in PBS and analysed at 575 and 440 nm by flow cytometry (FACS).

Redistribution of plasma membrane phosphatidylserine was assessed using Annexin V-FITC (Pharmingen, San Diego, Calif.). Cells suspended in 500 ul 10 mM Hepes, pH 7.4, 140 mM NaCl, 2.5 mM CaCl2 containing 2.5 ug/ml Annexin V-FITC were incubated in the dark at room temperature for 20 minutes, 200 ng/ml DAPI added and the cells analysed at 540 nm and 440 nm by flow cytometry (FACS).

Caspase 3 activity was measured by cleavage of non fluorescent PhiPhiLux to a fluorescent product (OncoImmunin, Mass.). Cells in suspension in 500 µl 30 µM PhiPhiLux in PBS were incubated at 37° C. for 60 minutes, washed twice with PBS and resuspended in 300 µl PBS containing 200 ng/ml DAPI and analysed at 575 nm and 440 nm.

Strand break DNA fragmentation was analysed by terminal deoxynucleotidyl transferase (TdT)-mediated dUTP nick end labelling (TUNEL) using the Apo-Brdu kit (Phoenix Flow Systems, Phoenix, Ariz.) according to the manufacturers instructions and analysed using a FACS Calibur (Becton Dickinson, San Jose, Calif.).

PI3 kinase assay: Competitive ELISA was used to assess PI3 kinase activity at time points of 0, 6, 12, 18, and 24 hours from seeding. 30 nM βGBP was added to cells at 3 hours after seeding. Assays were performed in triplicate.

$5 \times 10^6$ cells were washed three times with 137 mM NaCl, 20 mM Tris HCl pH7.4, 1 mM CaCl$_2$, 1 mM MgCl$_2$, 0.1 mM Na orthovanadate (Sigma, UK) (Buffer A) and lysed in 1 ml of the same buffer supplemented with 1 mM PMSF (Sigma, UK) and 1% NP40 (Calbiochem, San Diego, Calif.) for 20 minutes on ice. Lysates were centrifuged at 13000 rpm for 10 minutes to remove insoluble material and the supernatants stored at −80° C.

Frozen lysates containing 600 µg protein were thawed on ice and PI3 kinase was immunoprecipitated by incubation with 5 µl anti-PI3 kinase p85 (Upstate Biotechnology, Lake Placid, N.Y.) for one hour at 4° C. on a rotating wheel, followed by addition of 60 µl of a 50% slurry of Protein A agarose (Sigma, UK) beads in PBS for one hour at 4° C. The immunoprecipitated enzyme was collected by centrifugation at 13000 rpm for 10 seconds. Pellets were washed three times in buffer A plus 1% NP40, three times in 0.1M Tris-HCl, pH 7.4, 5 mM LiCl, 0.1 mM Na orthovanadate and twice with 10 mM Tris-HCl, pH7.4, 150 mM NaCl, 5 mM EDTA, 0.1 mM Na orthovanadate.

Pellets resuspended in 110 µl kinase reaction buffer (5 mM HEPES pH 7.0, 2.5 mM MgCl2, 25 µM ATP) were incubated in a water bath for 3 hours at 37° C. with 40 pmol PI(4,5)P2 substrate (Echelon Biosciences, Salt Lake City, Utah). The reaction was stopped with EDTA at a final concentration of 5 mM and the reaction mixture centrifuged at 13000 rpm at 4° C.

Supernatants were transferred to a microtitre plate for a competitive ELISA (Echelon Biosciences K-1000, Salt Lake City, Utah) to quantify the PI(3,4,5)P3 generated in the kinase reaction. Duplicate 50 µl volumes of the supernatants were each incubated with 50 µl of anti PI(3,4,5)P3 antibody for 1 hour at room temperature. The reaction mixture was then transferred to a microtitre plate coated with PI(3,4,5)P3 and incubated for 1 hour in the dark. After 3 washes with TBS plus 0.05% Tween 20 (Sigma, UK), 100 µl of HRP conjugated antibody to the anti PI(3,4,5)P3 was added to each well and incubated for 1 hour at room temperature in the dark. Following 3 further washes with TBS plus 0.05% Tween 20, 100 µl of TMB substrate (Echelon Biosciences, Salt Lake City, Utah) was added and the reaction was stopped after an appropriate time (~20 minutes) with 100 µl 0.5M H$_2$SO$_4$.

Absorbance of the samples was measured at 450 nm and the PI(3,4,5)P3 was quantified by comparison with a PI(3,4,5)P3 standard curve. Readings to derive the standard curve were obtained from an ELISA using PIP3 standard concentrations on in parallel with the ELISA of the experimental samples. The standard curve (not shown) was plotted on a log scale. The PI(3,4,5)P3 concentrations obtained for the experimental samples were thus available for direct comparison to the PIP3 standard curve. The experimental samples included samples from control cells and samples from cells treated with βGBP.

Northern blot analysis: Total RNA was extracted from cells using Trizol reagent (Invitrogen, UK) according to the manufacturer's instructions. 10 μg RNA was run on 2.2M formaldehyde-1.25% agarose gels. Akt mRNA was assessed using a cDNA probe (HA.Akt) which recognizes akt gene 1, 2, and 3. A GAPDH cDNA) was used for RNA loading control.

Western blot analysis: Cells were lysed in 50 mM Tris pH7.4. 150 mM NaCl, 1% TritonX-100, 1 mMPMSF, 2.5 μg/ml leupeptin, 1% aprotinin, 10 mM sodium fluoride, 1 mM sodium vanadate (Sigma, UK). 50 μg of protein were loaded onto 12% polyacrylamide gels. Phosphorylated Akt was detected using 1:1000 anti-phospho-Akt (Ser473) antibody (Cell Signalling Technology, Boston, Mass.) and total Akt1/2 protein was probed with 1:1000 anti-Akt1/2 (H136) (Santa Cruz, Santa Cruz, Calif.). Secondary antibodies conjugated to horseradish peroxidase (HRP) (GE Healthcare, UK) were used at 1:1000 dilution and visualised by enhanced chemiluminescence (GE Healthcare, UK). Actin (Sigma, UK) was used as a loading control.

The results shown in FIG. 1.

Example 2

Changes in Mitogenic Input in Non-Cancerous Cells and Response to Treatment with βGBP Cell culture: MCF10A, MCF10A$^{V12Ras}$ and MCF10A$^{CTx}$ cells were grown in DMEM/F12 medium plus 5% horse serum (Invitrogen UK), 10 ug/ml insulin, 5 μg/ml hydrocortisone (Calbiochem, San Diego, Calif.) and 20 μg/ml epidermal growth factor (Calbiochem, San Diego, Calif.), plus 100 ng/ml cholera toxin (Sigma, UK) in the case of the MCF10A$^{CTx}$ cells. Cultures were incubated at 37° C. in a humidified atmosphere of 5% CO2 in air.

Growth rates: Cells were removed from the flasks by trypsinisation and counted in a haemocytometer to assess cell numbers at time points of 1, 2, 3, 4, and 5 days for MCF10A$^{V12Ras}$ cells and MCF10A$^{CTx}$ cells. MCF10A cells were monitored at 1, 2, 3, and 4 days. Cell numbers were determined in triplicate by counting trypsinised cells in a haemocytometer.

βGBP: Hu-r-βGBP was obtained as described in Example 1 and added to cell cultures at a concentration of 15 nM or 30 nM at hour 3 after seeding cells. Control cells (0 nM βGBP) were also prepared. Hu-r-βGBP was maintained at the appropriate concentration (0 nM, 15 nM or 30 nM respectively) throughout the time course of the cell culture.

Cytofluorimetry: Apoptosis was monitored by reference to Annexin V as described in Example 1. Cells were analysed at a time point of 3 days. Redistribution of plasma membrane phosphatidylserine was assessed using Annexin V-FITC (Pharmingen, San Diego, Calif.). Cells suspended in 500 ul 10 mM Hepes, pH 7.4, 140 mM NaCl, 2.5 mM CaCl$_2$ containing 2.5 ug/ml Annexin V-FITC were incubated in the dark at room temperature for 20 minutes, 200 ng/ml DAPI added and the cells analysed at 540 nm and 440 nm.

PI3 kinase assays, Northern and Western blot analysis were carried out on these cells as already described in Example 1.

The results are shown in FIG. 2.

Example 3

ERK Levels as a Reflection of Endogenous and Enforced Mitogenic Input

Cell culture: BT474, SKBR3, MCF10A, MCF10AV12Ras and MCF10ACTx cells were cultured as described in Examples 2 and 3. No βGBP was included in the culture medium. Cells were harvested at 2 days from seeding, except for SKBR3 cells which were harvested at 3 days from seeding.

Western blot analysis: Total levels of ERK1 and ERK2, and phosphorylated levels of ERK1 and ERK2 were assessed by western blotting using the same protocol as described in Example 1.

Phosphorylated ERK1/2 were probed with 1:1000 anti-phospho-p44 ERK 1 and p42 ERK 2 monoclonal antibody (Cell Signalling Technology, Boston, Mass.). Non phosphorylated ERK1/2 proteins were probed with 1:1000 anti-ERK2 (Santa Cruz, Santa Cruz, Calif.) which recognises both p44 ERK 1 and p44 ERK 2. Actin (Sigma, UK) was used as a loading control.

Figure 3:
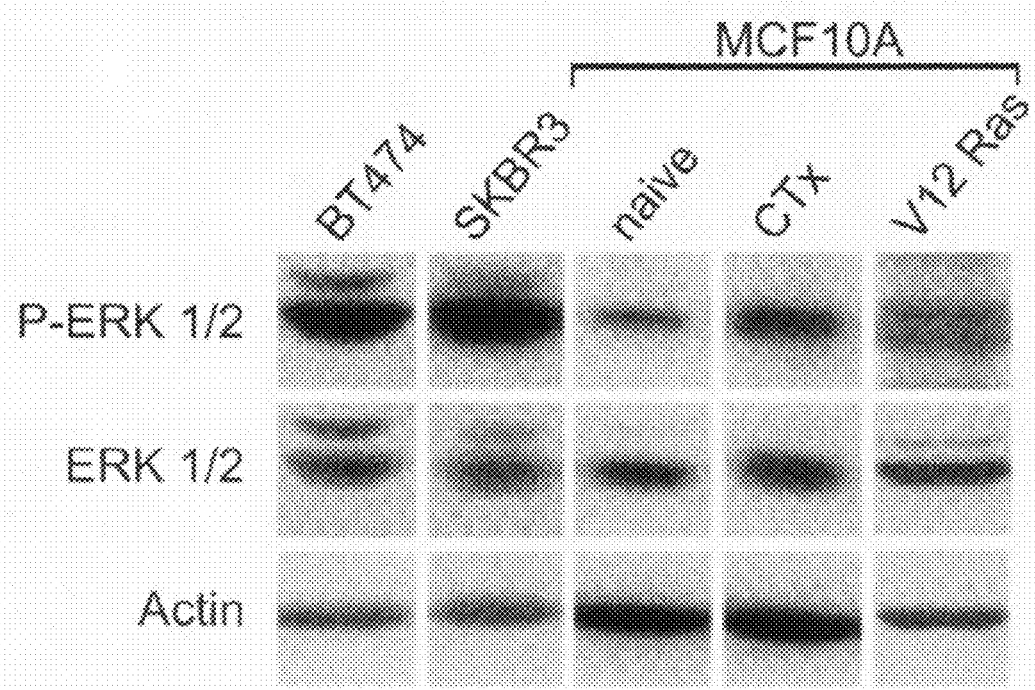
FIG. 3 shows ERK levels as a reflection of endogenous and enforced mitogenic input. Phosphorylated ERK and total ERK protein assessed at day 2 or day 3 (SKBR3) during mitogenic expansion.
Figure 4A:
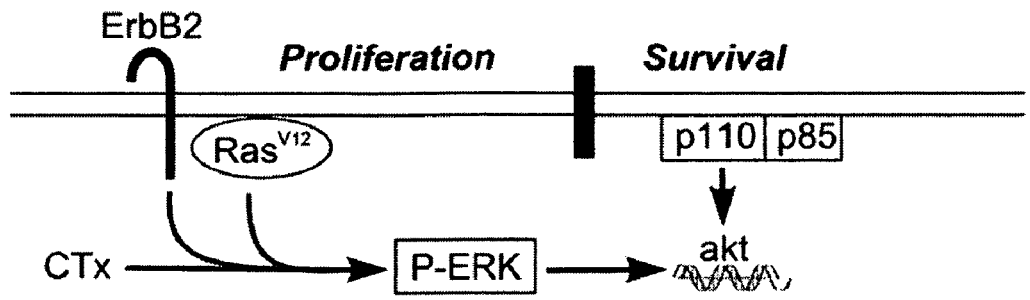
(FIG. 4A) Strong mitogenic signalling raises ERK activity and akt gene expression, for which PI3K activity is a requirement, to foster cell proliferation and survival. Further to ErbB2 and Ras, it is expected that overexpression of other oncogenes will elicit the same effect.
Figure 4B:
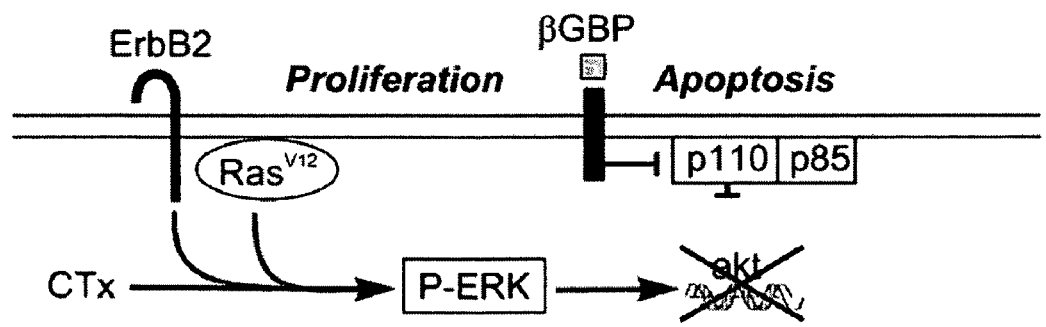
(FIG. 4B) While cell proliferation continues to be enforced by strong mitogenic signalling, inhibition of PI3K activity by ☐GBP leads to loss of akt gene function and to apoptotic death.

The results are shown in FIG. 3.

Example 4

Response of MCF-7 Cells to Raised Mitogenic Input and to Treatment with Hu-r-βGBP Cell culture: In the following procedures MCF-7 cells were grown in RPMI medium with 10% fetal calf serum (Invitrogen, UK). MCF-7$^{CTx}$ cells were grown under the same conditions with the addition of Cholera toxin at 100 ng/ml. Where required, Hu-r-βGBP was obtained as described above Example 2.

ERK levels: The effect of Cholera toxin at 100 ng/ml on ERK levels was assessed and compared with control cells cultured in the absence of the Cholera toxin after 2 days. Western blotting was carried out on MCF-7 cells harvested after 2 days, cultured in the presence or absence of cholera toxin. Western blotting to detect ERK1 and ERK2 and phosphorylated ERK1 and phosphorylated ERK2 was carried out as described above in Examples 1 and 3.

Growth rates: Cell numbers were measured over a time course of 4 days. Cell numbers were assessed at 0, 1, 2, 3, 4 days for MCF-7 cells incubated in the presence or absence of Cholera toxin at 100 ng/ml. Cell numbers were assessed in triplicate by haemocytometer counting as discussed above in Example 1.

Northern blot analysis: Cellular mRNA levels were analysed as discussed above in Example 1. akt mRNA levels were assessed after MCF-7 cells had been cultured with Cholera toxin at 100 ng/ml at time points of 1, 2 and 3 days. GADPH mRNA was used as a loading control as previously. Results were compared with control MCF-7 cells which had been cultured in the absence of Cholera toxin.

Growth rates in response to βGBP: Cell numbers were measured over a time course of 6 days. Cell numbers were assessed at 0, 1, 2, 3, 4, 5 and 6 days for MCF-7 cells incubated in the presence or absence of Cholera toxin at 100 ng/ml.

Hu-r-βGBP was added to these cell cultures at a concentration of 20 nM at hour 3 after seeding cells. Hu-r-βGBP was maintained throughout the time course of the cell culture.

Cell numbers were assessed in triplicate by haemocytometer counting as discussed above in Example 1.

Relationship between down regulation of PI3 kinase activity and akt mRNA levels: MCF-7 cells were cultured as discussed above. Cells were treated with 20 nM Hu-r-βGBP, 10 nM wortmannin or 20 nM LY294002 added at hour 3 from seeding.

PIP3 levels and akt mRNA levels were measured in these cells at time points of 6, 12, 18 and 24 hours from seeding.

PIP3 values were assessed in triplicate according to the protocol for the PI3 kinase assay described in Example 1. Cellular mRNA levels were analysed following the Northern blotting protocol described above in Example 1.

The results are shown in FIG. 5.

Example 4

In Vivo Efficacy and Safety

Female SCID mice were housed under standard conditions. Mice were divided into four groups of four. At age 6 weeks $5 \times 10^6$ ST4 (Human malignant T cell leukaemia) cells were injected subcutaneously (day 0).

Hu-r-βGBP was obtained as described in Example 1.

βGBP was administered from day 1 to day 16 by individual daily subcutaneous injection. Each group of mice received a different dosage of βGBP. 0 ng/mouse (control), 20 ng/mouse, 200 ng/mouse or 400 ng/mouse Tumour size was assessed at day 42 or day 90 by calliper measurement.

The results are shown in Table 1.

Example 5

Effect of βGBP on Colon Cancer Cells

Cell culture: SW480, SW620 and LoVo colon cancer cells were grown in Leibowitz L-15 medium with 10% fetal bovine serum in sealed flasks at 37° C. Hu-r-βGBP was added 3 hrs after seeding cells at a concentration of 1 nM or 2 nM. Control cells were grown without βGBP.

Growth rates: Cell numbers were measured over a time course of 5 days. Cell numbers were assessed at 0, 1, 2, 3, 4, and 5 days for each cell type incubated in the presence of Hu-r-βGBP. Cell numbers were assessed in triplicate by counting in a haemocytometer as discussed above in Example 1 and compared with cell numbers for control cells grown without βGBP.

The results are shown in FIG. 6.

REFERENCES

Alberts B, Johnson A, Raff M, Roberts K, Walter P (2002) In *Molecular Biology of the Cell*, (Garland Science, New York), pp 845-856.
Aurias A, Rimbaut C, Buffe D, Zucker J M, Mazabraud A (1984) *Cancer Genet Cytogenet* 12: 21-25.
Baldini A, Gress, T, Patel K, Muresu R, Chiariotti L, Williamson P, Boyd L, Casciano 1, Wells V, Bruni C et al. (1993) *Genomics* 15: 216-218.
Baselga J (2006) *Science* 312: 1175-1178.
Blaser C, Kaufman M, Muller C, Zimmermann C, Wells V, Mallucci L, Pircher H (1998) *Eur J Immunol* 28: 2311-2319.
Bos J L (1989) *Cancer Res* 49: 4682-4689.
Bridge J A, Borek D A, Neff J R, Huntrakoon M (1990) *Am J Clin Pathol* 93: 26-31.
Chang F, Lee J T, Navolanic P M, Steelman L S, Blalock W L, Franklin R A, McCubrey J A (2003) *Leukemia* 17:590-603.
Chen Y L, Law P Y, Loh H H (2005) *Curr Med Chem Anticancer Agents* 5: 575-589.
Chiariotti L, Wells V, Bruni C B, Mallucci L (1991) *Biochim BiophysActa* 1089: 54-60.
Dankart D L, Wang Z, Blackmore V, Moran M F, Muller W J (1997) *Mol Cell Biol* 17: 5410-5425.
Djodjevic S, Driscoll P (2002) *Trends in Biochem Sci* 27: 426-433.
Downward J (2003) *Nature Rev.* 3: 11-22.
Foukas L C, Claret M, Pearce W, Okkenhauq K, Meek S, Peskett E, Sancho S, Smith A J, Withers D J, Vanhaesebroeck B (2006) *Nature* 441: 366-370.
Georgakis G V, Younes A (2006) *Expert Rev Anticancer Ther* 6: 131-140.
Gibbs J B (2000) *Science* 287: 1969-1973.
Harari D, Yarden Y (2000) *Oncogene* 19: 6102-6114.
Hennessy B T, Smith D L, Ram P T, Lu Y, Mills G B (2005) *Nature Rev Drug Disc* 4: 988-1004.
Hirabayashi J, Ayaki H, Soma G, Kasai, J (1989) *FEBS Lett* 250: 161-165.
Hynes N E, Gerber H A, Saurer S, Groner B (1989) *J Cell Biochem* 39: 169-173.
Hynes N E, Stern D F (1994) *Biochim Biophys. Acta* 1198: 165-184.
Johnstone R W, Ruefli A A, Lowe S W (2002). *Cell* 108: 153-164.
Karanugaran D, Tzahar, E, Beerli R R, Chen X, Graus-Porter D, Ratzkin B J, Seger R, Hynes N E, Yarden Y (1996) *EMBO J* 15: 254-264.
Karin M, Hunter T (1995) *Current Biology* 5: 747-757.
Lu Y, Wang H, Mills G B (2003) *Rev Clin Exp Haematol* 7: 205-228.
Luo J, Manning B D, Cantley L C (2003) *Cancer Cell* 4: 257-262.
Mallucci L, Wells V (2005) *Curr Opin Investig Drugs* 6: 12228-12233.
Mallucci L, Wells V, Danikas A, Davies D (2003) *Biochem Pharmacol* 66: 1563-1569.
Mendelsohn, J, Baselga, J (2000) *Oncogene* 19: 6550-6566.
Mitin N, Rossmann K L, Derr, C. J (2005) *Curr Biol* 15: R563-R574.
Morgensztem D, McCleod HL (2005) *Anticancer Drugs* 16: 747-803.
Pacold M E, Suire S, Perisic O, Lara-Gonzalez S, Davis C T, Walker E H, Hawkins P T, Stephens L, Eccieston J F, Williams, RL (2000) *Cell* 103: 931-943.
Powis G, Bonjouklian R, Berggren M M, Gallegos A, Abraham R, Ashendel C, Zalkow L, Matter W F, Dodge J, Grindley G et al. (1994) *Cancer Res* 59: 2419-2423.
Rabinovich G A, Daly G, Dreja H, Tailor H, Riera C M, Hirabayashi J, Chemajovsky Y (1999) *J. Exp. Med.* 190: 385-397
Rabinovich G A, Iglesias M M, Modesti N M, Castagna L F, Todel C W, Riera C M, Sotmayor C E (1998) *J. Immunol.* 160: 4831-4840.
Rabinovich G A, Modesti N M, Castagna L F, Landa C A, Riera C M, Sotmayor C E (1997) *J. Biochem.* 122: 365-367.
Ravatn R, Wells V, Nelson L, Vettori D, Mallucci L, Chin K V (2005) *Cancer Res* 65: 1631-1634.
Repasky G A, Chenette E J, Der C J (2004) *Trends in Cell Biol* 14: 639-647.
Rey J A, Bello, M J, de Campos J. M, Vaquero J, Kusak M E, Sarasa J L, Pestana A (1993) *Cancer Genet Cytogenet* 66: 1-10.

Rodriguez-Viciana P, Warne P H Khwaja A, Marte B M, Pappin D, Das P, Waterfield M D, Ridley A, Downward J (1997) *Cell* 89: 457-467.

Rodriguez-Viciana P, Warne P H, Dhand R, Vanhaesebroeck B, Gout I, Fry, M J, Waterfield, Md., Downward J. (1994) *Nature* 370: 527-532.

Segatto O, Lonardo F, Pierce J H, Bottaro D P, Di Fiore P P (1990) *Nature New Biol* 2: 187-195.

Shulze A, Lehmann K, Jeffries H B J, McMahon M, Downward J (2001) *Genes Develop* 15: 981-984.

Sjoblom T, Jones S, Wood L D, Parsons D W, Lin J, Barber T D, Mandelker D, Leary R J, Ptak J, Silliman N et al. (2006) *Science* 314: 268-274.

Soule H D, Maloney T M, Wolman S R, Petersen W D, Brenz R, McGrath C M, Russo J, Pauley R J, Jones R F, Brooks S C (1990) *Cancer Res* 50: 6075-6086.

Turc-Carel C, Dal Cin P, Rao U, Karakousis C, Sandberg A A (1998) *Cancer Genet Cytogenet* 30: 145-150.

Vanhaesenbroeck B, Leevers S, Ahmadi K, Timms J, Katso R, Driscoll P C, Woscholski R, Parker P, Waterfield Md. (2001)*Ann Rev Biochem* 70: 535-602.

Vivanco I, Sawyers C L (2002) *Nature Reviews Cancer* 2: 489-501.

Vlahos C J, Matter W T, Hui K. Y, Brown F (1994) *J Biol Chem* 269: 5241-5248.

Walker E H, Pacold M E, Perisic O, Stephens L, Hawkins P T, Wymann M P, Williams R O (2000) *Mol Cell* 6: 909-919.

Wells V, Mallucci L (1991) *Cell* 64: 91-97.

Wennstrom S, Downward, J (1999) *Mol. Cell. Biol* 19: 727-736.

Wymann M P (1996) *Mol Cell Biol* 16: 1722-1733.

Yu D, Hung M C (2000) *Oncogene* 19: 6115-6121.

The invention claimed is:

1. A method for the prevention or treatment of cancer in a mammal, wherein said cancer is one which comprises cells in respect of which the effect of βGBP is not inhibition of growth and wherein said cells
    a) show elevated levels of akt gene expression and phosphorylated Akt protein compared to a control cell and/or
    b) show elevated ERK compared to a control cell and/or
    c) over-express ErbB2
said method comprising administering to said mammal an effective amount of βGBP whereby said cancer is prevented or treated.

2. The method of claim 1 wherein the effective amount of βGBP promotes apoptosis of the cells.

3. The method of claim 1 wherein the prevention or treatment of the cancer further comprises the administration or co-administration of a mitogen, or wherein βGBP is provided in a composition further comprising a mitogen.

4. The method of claim 3 wherein the mitogen
    a) is a hormone, or
    b) is a growth factor.

5. The method of claim 4 wherein the mitogen is
    a) a hormone and the hormone is an estrogen or an androgen,
    b) a growth factor which binds a tyrosine kinase receptor, or
    c) a growth factor which binds a G protein coupled receptor.

6. A method for the prevention or treatment of a condition in which disease-associated cell division occurs in a mammal, wherein the cells which result from said disease associated cell division comprise a cell in respect of which the effect of βGBP is not inhibition of growth, or wherein the cells which result from said disease associated cell division are mitogenically stimulated, comprising administering a mitogen in combination with or coadministered with βGBP and wherein said condition is prevented or treated.

7. The method of claim 6 wherein the condition is cancer, an immune condition, or an inflammatory condition.

8. The method of claim 7 wherein the condition is cancer and the cancer is colon cancer, and wherein a single dose of the βGBP is sufficient to achieve a concentration of βGBP in the mammal of 15-150 µg/kg.

9. The method of claim 7 wherein the condition is cancer and the cancer is colon cancer, and wherein a single dose of the medicament or coadministered βGBP is sufficient to achieve a concentration of βGBP in the mammal of 15-60 µg/kg.

10. The method of claim 7 wherein the condition is an immune condition and the immune condition is an autoimmune condition, is an alloimmune condition, comprises an immune reaction to a graft, comprises an immune reaction by a graft, comprises a hypersensitivity reaction, or comprises the persistent proliferation of activated lymphocytes.

11. The method of claim 6 wherein the cells which result from said disease associated cell division comprise a cell which has a high intrinsic mitogenic capacity, is mitogenically stimulated, is a rapidly dividing cell, or is a persistently dividing cell.

12. The method of claim 6 wherein the cells which result from said disease associated cell division comprise a cell which is or is suspected of being a hyperproliferative cell, a neoplastic cell, a cancer cell, an activated lymphocyte, an activated T cell, an activated B cell, a persistently dividing lymphocyte, an activated inflammatory cell, or an activated endothelial cell.

13. The method of claim 6 wherein the mitogen
    a) is a hormone,
    b) is a growth factor, or
    c) is or comprises an antigenic determinant which binds to a receptor on a immune cell.

14. The method of claim 13 wherein the mitogen is
    a) a hormone and the hormone is an estrogen or an androgen,
    b) a growth factor which binds a tyrosine kinase receptor,
    c) a growth factor which binds a G protein coupled receptor, or
    d) an antigenic determinant which binds to a receptor on a immune cell and wherein the receptor is a T cell receptor (TCR), an antibody, or an MHC molecule.

15. The method of claim 6 wherein the administration of βGBP and a mitogen promotes apoptosis of the cells which result from said disease associated cell division.

16. A method for the prevention or treatment of a condition in which disease-associated cell division occurs in a mammal, wherein the cells which result from said disease-associated cell division comprise a cell in respect of which the effect of βGBP is not inhibition of growth, or wherein the cells which result from said disease-associated cell division are mitogenically stimulated, wherein said condition is an autoimmune condition, is an alloimmune condition, an immune reaction to a graft, an immune reaction by a graft, a hypersensitivity reaction, or the persistent proliferation of activated lymphocytes and wherein said method comprises administering βGBP at a concentration from 0.1 to 50 nanomolar, whereby said condition is prevented or treated.

17. The method of claim 16 wherein the cells which result from said disease associated cell division comprise a cell which has a high intrinsic mitogenic capacity, is mitogenically stimulated, is a rapidly dividing cell, or is a persistently dividing cell.

18. The method of claim 16 wherein the cell which results from said disease associated cell division comprise a cell which is or is suspected of being an activated lymphocyte, an activated T cell, an activated B cell, persistently dividing lymphocyte, an activated inflammatory cell, or an activated endothelial cell.

19. The method of claim 16 wherein βGBP promotes apoptosis of the cells which result from said disease-associated cell division.

20. The method of claim 16 wherein the prevention or treatment of the condition further comprises the administration or co-administration of a mitogen, or wherein βGBP is provided in a composition further comprising a mitogen.

21. The method of claim 20 wherein the mitogen is or comprises an antigenic determinant which binds to a receptor on a immune cell.

22. The method of claim 21 wherein the mitogen in an antigenic determinant which binds to a receptor on a immune cell and wherein the receptor is a T cell receptor (TCR), an antibody, or an MHC molecule.

23. A pharmaceutical composition comprising a therapeutically effective amount of βGBP and a therapeutically effective amount of a mitogen for use in the treatment of a condition in which disease associated cell division occurs, wherein the cells which result from said disease associated cell division comprise a cell in respect of which the effect of βGBP is not inhibition of growth, or wherein the cells which result from said disease associated cell division are mitogenically stimulated.

24. The pharmaceutical composition of claim 23 wherein the mitogen
    a) is a hormone,
    b) is a growth factor, or
    c) is or comprises an antigenic determinant which binds to a receptor on a lymphocyte.

25. The pharmaceutical composition of claim 24 wherein the mitogen is
    a) a hormone and the hormone is an estrogen, an androgen,
    b) a growth factor which binds a tyrosine kinase receptor,
    c) a growth factor which binds a G protein coupled receptor, or
    d) an antigenic determinant which binds to a receptor on a immune cell and wherein the receptor is a T cell receptor (TCR), an antibody, or an MHC molecule.

26. The pharmaceutical composition of claim 23 wherein the composition is formulated in individual unit dose form, and wherein a single dose of βGBP is sufficient to achieve a concentration in the subject of 15-150 µg/kg.

27. The pharmaceutical composition of claim 23 wherein the composition is formulated in individual unit dose form, and wherein a single dose of βGBP is sufficient to achieve a concentration in the subject of 15-60 µg/kg.

* * * * *